US012667636B2

(12) United States Patent
Vincent et al.

(10) Patent No.: US 12,667,636 B2
(45) Date of Patent: Jun. 30, 2026

(54) APPARATUS FOR IRRADIATING GOODS LOADED IN TOTES

(71) Applicant: Ion Beam Applications, Louvain-la-Neuve (BE)

(72) Inventors: Dominique Vincent, Louvain-la-Neuve (BE); Frédéric Dessy, Louvain-la-Neuve (BE); Jérémy Brison, Louvain-la-Neuve (BE); Frédéric Stichelbaut, Louvain-la-Neuve (BE)

(73) Assignee: Ion Beam Applications, Louvain-la-Neuve (BE)

( * ) Notice: Subject to any disclaimer, the term of this patent is extended or adjusted under 35 U.S.C. 154(b) by 1012 days.

(21) Appl. No.: 17/726,797

(22) Filed: Apr. 22, 2022

(65) Prior Publication Data

US 2022/0339310 A1     Oct. 27, 2022

(30) Foreign Application Priority Data

Apr. 27, 2021    (EP) ..................................... 21170600

(51) Int. Cl.
*A61L 2/24*          (2006.01)
*A61L 2/08*          (2006.01)
            (Continued)

(52) U.S. Cl.
CPC ................. *A61L 2/24* (2013.01); *A61L 2/082* (2013.01); *A61L 2/087* (2013.01); *A61L 2202/14* (2013.01); *A61L 2202/23* (2013.01)

(58) Field of Classification Search
CPC . G21K 5/08; A61L 2/082; A61L 2/087; A61L 2/24; A61L 2202/14; A61L 2202/23; B65B 55/16; B65B 55/08
See application file for complete search history.

(56) References Cited

U.S. PATENT DOCUMENTS

| | | | | |
|---|---|---|---|---|
| 3,641,342 A | * | 2/1972 | Armel | ...................... A61L 2/24 |
| | | | | 976/DIG. 441 |
| 3,676,675 A | * | 7/1972 | Ransohoff | ................ G21K 5/02 |
| | | | | 976/DIG. 441 |

(Continued)

FOREIGN PATENT DOCUMENTS

EP          3378497 A1      9/2018

OTHER PUBLICATIONS

European Search Report in counterpart European Application No. 21170600.7 dated Oct. 18, 2021 (9 pages).

*Primary Examiner* — David J Makiya
*Assistant Examiner* — Soorena Kefayati
(74) *Attorney, Agent, or Firm* — Finnegan, Henderson, Farabow, Garrett & Dunner, LLP

(57) ABSTRACT

An apparatus includes a radiation source configured to emit a radiation along an irradiation volume, and a conveyor configured to drive goods loaded in two or more transport units through the irradiation volume so as to expose a first portion of the goods to the radiation. The transport units may be loaded in totes of a tote height, and the conveyor may be configured to drive the totes. The totes may be arranged on top of one another, and each transport unit may be held in place in a tote by one or more support elements such that a total height of the totes is between 40% and 100% of the tote height, the transport units are loaded in a tote span over at least 70% of the total height, and the total height is centered relative to the tote height within about 20%.

15 Claims, 11 Drawing Sheets

(51) Int. Cl.
    *A61L 2/082*         (2026.01)
    *A61L 2/087*         (2026.01)

(56)               References Cited

U.S. PATENT DOCUMENTS

| | | | | | |
|---|---|---|---|---|---|
| 4,481,652 | A | * | 11/1984 | Ransohoff | B65B 55/16 |
| | | | | | 378/69 |
| 4,864,595 | A | * | 9/1989 | Barrett | G21K 5/10 |
| | | | | | 378/68 |
| 5,001,352 | A | * | 3/1991 | Tetzlaff | A61L 2/081 |
| | | | | | 378/69 |
| 6,931,095 | B1 | * | 8/2005 | Koenck | G21K 5/10 |
| | | | | | 378/69 |
| 2007/0009090 | A1 | * | 1/2007 | Stichelbaut | G21K 5/10 |
| | | | | | 378/69 |
| 2013/0071527 | A1 | * | 3/2013 | Pesce | A23B 2/22 |
| | | | | | 99/451 |
| 2015/0108366 | A1 | * | 4/2015 | Kawasaki | A61L 2/08 |
| | | | | | 250/453.11 |
| 2017/0154751 | A1 | * | 6/2017 | Brown | H01J 37/141 |
| 2018/0344884 | A1 | * | 12/2018 | Kawasaki | B65B 55/08 |
| 2018/0358143 | A1 | * | 12/2018 | Kim | G21K 5/10 |
| 2021/0393835 | A1 | * | 12/2021 | Rosenblat | A61L 2/26 |
| 2022/0212878 | A1 | * | 7/2022 | Siegelin | A61L 2/081 |

\* cited by examiner

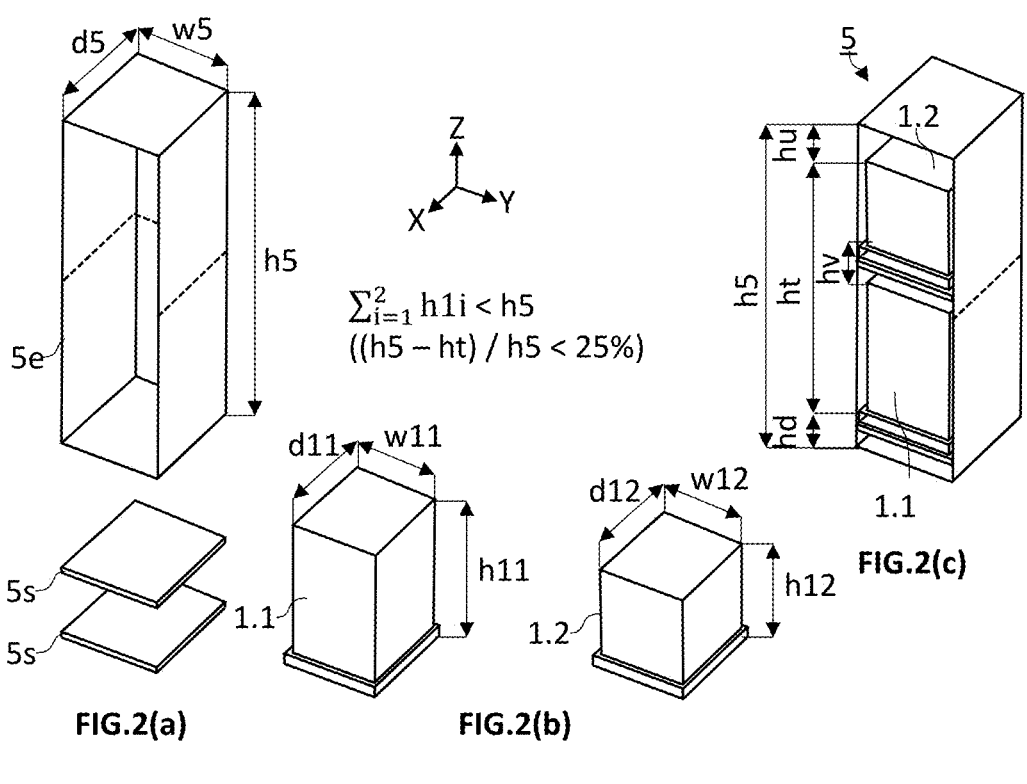
$$\sum_{i=1}^{2} h1i < h5$$
$$((h5 - ht) / h5 < 25\%)$$
FIG.2(a)        FIG.2(b)        FIG.2(c)
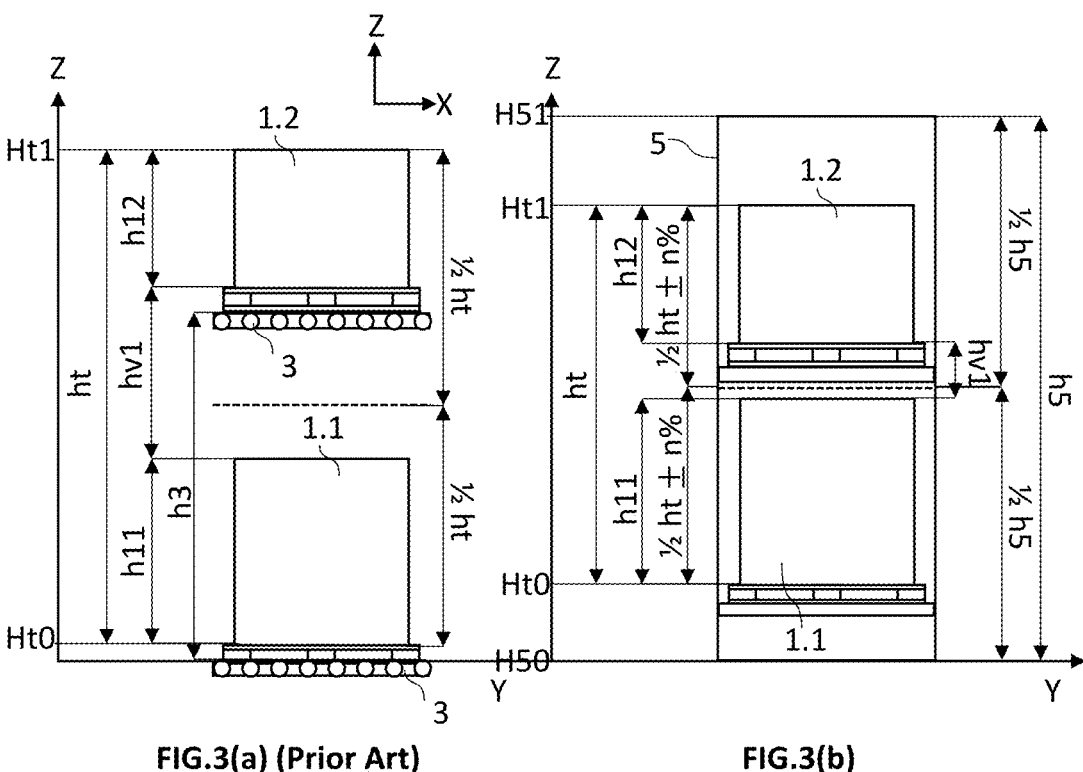
FIG.3(a) (Prior Art)        FIG.3(b)

h11 = h12 = 260 cm, hx = 300 cm h1.1 = 100 cm, w1.1 = 300 cm, ρ = 0.1 g/cm³

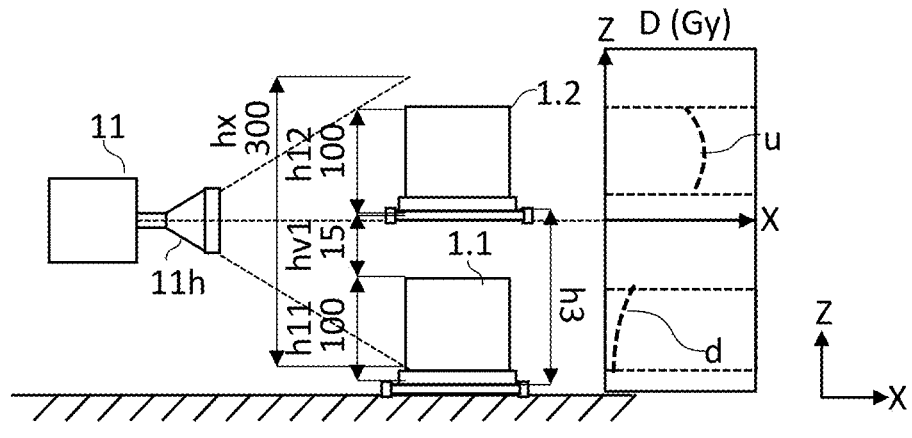
FIG.9(a) (Prior Art)
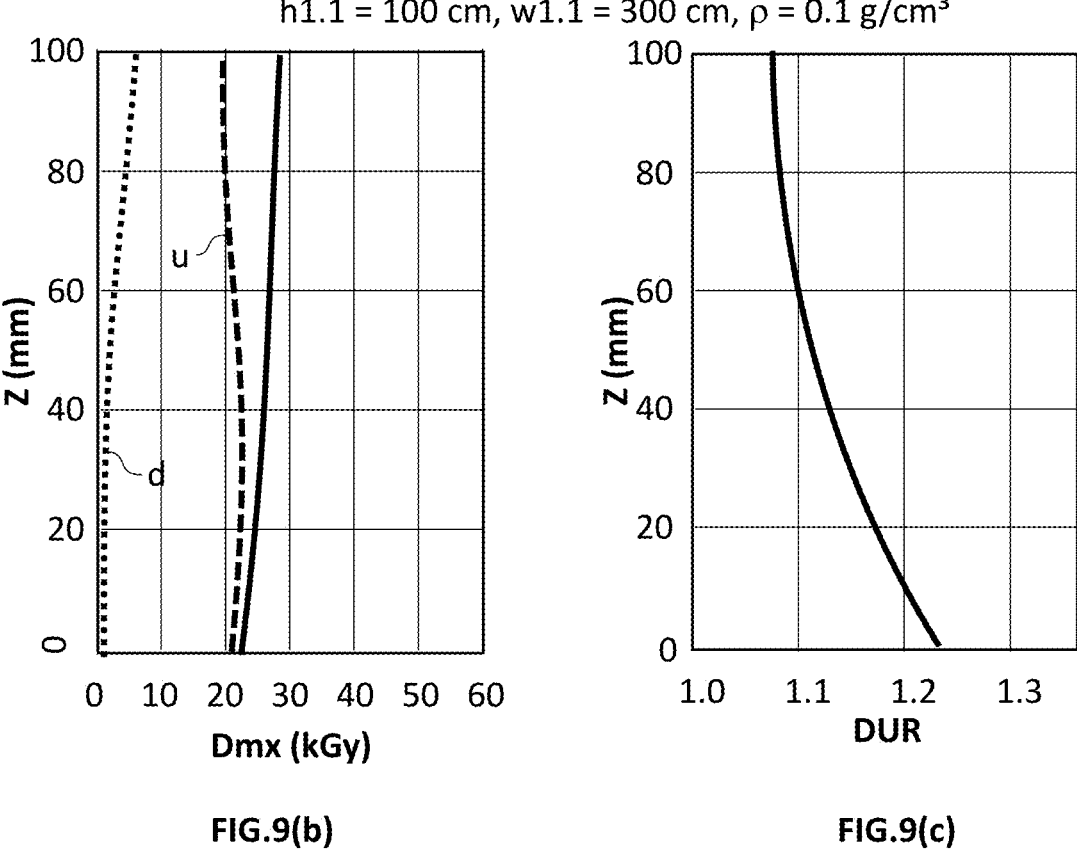
FIG.9(b)                    FIG.9(c)

h1.1 = 100 cm, w1.1 = 300 cm, ρ = 0.1 g/cm³

APPARATUS FOR IRRADIATING GOODS LOADED IN TOTES

CROSS-REFERENCE TO RELATED PATENT APPLICATIONS

This application claims foreign priority of European Patent Application No. 21170600.7, filed Apr. 27, 2021, which is hereby incorporated by reference in its entirety.

TECHNICAL FIELD

The present disclosure relates to an apparatus for irradiating goods with a radiation selected from X-rays or electron beam ensuring an enhanced throughput and, at the same time, an enhanced homogeneity of radiation and energy efficiency than with state-of-the-art apparatuses. This is made possible by loading the goods in totes according to certain constraints of positioning and distributing the goods along a vertical axis (Z) in the totes. The totes carrying the goods are driven through an irradiation volume by a conveyor.

BACKGROUND

Irradiation of goods with X-rays or an electron beam has been used for different purposes, including sterilisation, cross-linking of resins and paints, shrink-fitting polymer sheets or tubes, such as sheaths about electric cables, and the like. X-ray or electron beam sterilisation of medical devices, tools, and garments, and sterilisation of foodstuff have been reported in the art. X-ray-sterilisation is advantageous over other types of sterilisation techniques such as y-irradiation-, or ethylene oxide-sterilisation techniques, in that X-rays can penetrate deeply full pallets and containers with densities of up to 1.0 g/cm³, which is higher than the foregoing techniques. X-ray sterilisation has a very high tolerance to density variations.

X-rays are a high-energy electromagnetic radiation. Most X-rays have a wavelength ranging from 10 $\mu$m to 10 nm, corresponding to frequencies in the range $3\times10^{16}$ Hz to $3\times10^{19}$ Hz. One common practice is to distinguish X-radiation from y-radiation on the basis of their source: X-rays are emitted by the interaction of accelerated electrons with a target, such as a high-Z metal, while y-rays are emitted by an atomic nucleus, such as Cobalt 60. The energy of the photons emitted by Cobalt-60 is measured at 1.17 MeV and 1.33 MeV. These high energy photons are emitted in all directions, or in an isotropic fashion. The energy of X-rays is directly related to the electron energy. X-rays are generated by interacting accelerated (energetic) electrons with atoms in a target material. As high energy electrons pass in the vicinity of a nucleus all or part of the electron's energy is dissociated from it and propagates in space as electromagnetic radiation (=X-ray). The heavier the element (i.e., higher atomic number or 2-value), the greater the X-rays' conversion efficiency. Metals such as Tantalum (Ta) or Tungsten (W) are typically used as target material. The resulting X-ray energy spectrum ranges from zero up to the maximum of the incident electron energy. The design of the converter plays an important role in the characteristics of the X-rays. The converter material (Z-value) and its thickness determine the yield and fine-tune the energy spectrum, respectively. Typically, industrial accelerators suitable for the present disclosure may be designed to produce electron energies up to 10 MeV. For example, industrial accelerators may be designed to produce about 5 to 7 MeV electrons to produce X-rays.

The energy of the electrons for both X-rays generation or for direct use of the electron beam can be increased by accelerating the electrons in an accelerator. The following accelerators are available on the market,

- L-band linacs (accelerating RF in the range of 1 GHz; single pass through multiple cavities; e.g. Impela)
- DC accelerators (direct current; e.g. Dynamitron)
- Rhodotron (an RF-type accelerator; multi-pass through a single cavity, e.g., TT200)

When the incident electron beam is <100 KeV for X-ray generation, the resulting photons are emitted equally in all directions. As the energy of the incident radiation is increased, the Bremsstrahlung radiation beam becomes more "forward peaked." In order to control the geometry of the irradiation volume emitted out of the converter (or target material), a scan horn (11h) is used, in the shape of an inverted funnel. The shape and dimensions of the scan horn determine the geometry and dimensions of an irradiation volume (Vx) generated by the source of X-rays provided with a specific scan horn.

Batches of goods to be irradiated with X-rays or an electron beam can be stacked on pallets or enclosed in containers. The containers can be self-supporting or can themselves be laid on top of pallets. Such batches of goods and pallets and/or containers are collectively referred to as "transport units." As illustrated in FIGS. 1(a) and 1(b), the transport units are generally conveyed in prior art systems on a conveyor driving them horizontally, along a transverse axis (Y), in front of a source of radiation (11) selected from X-rays and electron beam. The dose deposition distribution on the goods with such systems decreases rapidly by absorption along the irradiation axis (X), which the irradiation volume is centred on as well known in the art.

One way of quantifying the variation of the dose deposition distribution along a given direction or plane is to calculate a dose uniformity ratio (DURi) along said direction or plane, wherein DURi=DMi/Dmi, with DMi is the maximum dose and Dmi the minimum dose deposited along said direction, i=X, Y, or Z. A value of DUR=1⇔DMi=Dmi, defines a perfectly homogenous dose deposition distribution along a given direction i. The larger the value of DURi, the larger the variations of dose deposition along the direction i.

To date, two major alternative techniques are currently used: one-level and two-level irradiation systems. In the one-level irradiation system, illustrated in FIG. 1(a), the goods are aligned on a single conveyor on one level only and irradiated with an overscan, i.e., using a scan horn yielding an irradiation volume of height (hx) along the vertical axis (Z) which is larger than a unit height (h1i) of the transport units (1i). The one-level system is advantageous in that a single pass is required for irradiating a first portion of the goods (the remaining portions can be irradiated by rotating the goods and exposing a new portion to the radiation as explained in continuation). A larger scan horn is, however, required, which increases the cost of the installation accordingly.

A two-level system is illustrated in FIG. 1(b) and described in EP1738776. It requires two superimposed conveyor tracks arranged on top of one another for conveying the goods over two levels. The radiation is approximately centred at mid-level of a total height (ht) of two superimposed transport units driven by the bottom and top tracks, respectively, and arranged to underscan, i.e., using a scan horn yielding an irradiation volume of scanning width (hx) measured along the vertical axis (Z) which is lower than the total height (ht) of the transport units. The transport units which have been irradiated a first time as they were conveyed on a top or bottom conveyor are passed a second time for irradiation after inverting their positions between the top and bottom conveyors and inversely. Having to pass the transport units twice through the irradiation volume would intuitively suggest a decrease of the throughput by half compared with the one-level system. This is, however, not the case, since in two-level systems, two transport units are irradiated simultaneously at each pass. Furthermore, the DUR is reduced (i.e., enhanced) with two-level systems compared with one-level systems. The choice of using the one- or two-level system remains at the discretion and choice of the operator, depending on the equipment available, the type of goods to be treated, the type of process the irradiation is used for (sterilization, polymerization, etc.), and the like.

Since the conveyor(s) drive(s) the goods through the irradiation volume (Vx) at a controlled speed along the transverse axis (Y), the dose deposition distribution along the transverse axis (Y) of the conveyor is substantially constant, with a DURy along the transverse axis (Y) close to 1. The dose deposition distribution along the irradiation axis (X) (i.e., parallel to an irradiation axis), decreases with penetration depth, yielding a high value of DURx, as shown in FIG. 7(b), dashed lines. The value of the DURx can be reduced by rotating the goods about the vertical axis and driving them as often as necessary through the irradiation volume to expose a different portion of the goods to the radiation. The solid line in FIG. 7(b) shows the dose deposited along the irradiation axis (X) after two passes through the irradiation volume, exposing two opposite portions of the transport unit by rotation thereof by 180° (=sum of the two dashes lines). Alternatively, a second source of radiation can be provided (not shown) pointing to a surface of the transport units opposite the surface irradiated by the first source of radiation. The latter solution is advantageous in that the throughput is increased, but the purchase of a second source of radiation increases the cost of the installation accordingly.

The dose deposition distribution along the vertical axis (Z), however, varies substantially because the height of the transport units containing the goods can vary considerably from one transport unit to another. Since high energy X-rays propagate in a forward peaked pattern, higher X-ray doses are deposited into the goods at the level of the irradiation axis (X) and the X-ray doses deposited along the vertical axis (Z) decrease with increasing distance from the irradiation axis (X). Consequently, a variation of the height of the target units yields a substantial corresponding variation of the dose deposition distribution along the vertical axis (Z), thus increasing the values of the corresponding DURz's>>1 along the vertical axis (Z). The two-level system attenuates this dose deposition variation along the vertical axis (Z), but at the expense of substantial energy waste. A homogeneous dose deposition (i.e., DUR→1) is important in many applications because the whole volume of the goods must receive a minimum dose sufficient for fulfilling the goal of the irradiation process, such as sterilisation, cross-linking, and the like. This means that the minimum dose (Dmz) deposited onto a good must be at least equal to the sufficient dose. If the DURz=DMz/Dmz is >>1, the maximum dose (DMz) deposited in some portions of the goods may be too high for the integrity of the goods and said portions of the goods may be degraded by the excess of irradiation. It is therefore important to reduce the DURz and thus ensure that the DUR along all directions is sufficiently close to 1, e.g., DUR<1.4.

To minimize the value of DURz in the vertical direction in a one-level system as depicted in FIG. 1(a), the scan horn (11h) must be dimensioned such as to overscan beyond the boundaries of the target product, such as to deposit doses according to a relatively flat bottom segment of the approximately parabolic-shaped curve of dose deposition about the vertical axis (Z). In order to limit the size and the costs of the X-ray scan horn, the overscanning is generally limited to 20 to 30 cm beyond the transport unit boundaries. Since the unit height (h1i) of the transport units, however, can vary substantially from one transport unit to another, it is impossible to optimize the DURz with a single scan horn fitting all heights at a reasonable cost. Note that it is cumbersome and impractical to change scan horn between two target products.

The two-level system illustrated in FIGS. 1(b), 5(e) and 5(f) yields lower (better) values of DURz, by driving the goods twice through the irradiation volume in swapped positions along the vertical axis (Z). This way, although the DURz of the transport units in both bottom and top conveyors is quite high after the first pass, by swapping their positions in a second pass, the variations in doses deposition are inverted and compensate the variations accumulated during the first pass. The top and bottom conveyors are, however, at fixed positions, separated from one another by a fixed conveyors separation distance (h3) which cannot be amended. The conveyors separation distance (h3) has two main drawbacks. First, it defines an upper boundary of the unit height (h1i) of the transport units (h1i<h3) that can be driven by the bottom conveyor. Second, for transport units having a height (h1i) much lower than h3 (i.e. h1i<<h3), as shown in FIG. 5(g), there is a large gap between the top conveyor and a top of the transport unit driven by the bottom conveyor, where X-rays or electron beams are lost and must be contained, leading to considerable waste of energy. This can be quantified by an exposure ratio, $$\Sigma_{i=1}^{2} h1i / ht,$$

defined as a ratio of a sum of the unit heights (h11, h12) of the transport units (1.1, 1.2) carried by the bottom and top conveyor tracks, to the total height (ht). The larger the exposure ratio, the larger the portion of radiation hitting a transportation unit.

To lower (improve) the DURz, U.S. Pat. No. 6,504,898 discloses a rotation system where a product is rotated before the radiation source. A pallet is turned slowly about its vertical axis as the x-ray radiation is scanned up and down. A shutter apparatus consisting of a pair of x-ray absorbing doors is located between the scan horn x-ray conversion plate and pallet to shape the x-ray pattern and to attenuate the x-ray intensity during the times that the face of pallet is turned towards the scan horn.

A disadvantage of this x-ray irradiation system is that the shutter causes valuable X-ray energy to be converted into heat and be wasted. A further drawback is the dependence on precise mechanical movement and rotation of the target material being irradiated to achieve the desired dosage uniformity. The timing and control of shutter doors must be precisely mechanically synchronized with the rotation of the pallet on turntable to compensate for the varying material thickness.

U.S. Pat. No. 6,940,944 describes an apparatus for radiation processing of target products comprising a radiation source, a collimator having a variable aperture, and a turntable. The collimator is adapted for adjusting its aperture prior to irradiation of a package.

Alternative irradiation methods have been developed to irradiate a great variety of products of different densities with improved DUR. EP1459770 cited supra proposes a process where at least two pallets are loaded on rotation means for simultaneous irradiation. EP1738776 discussed supra discloses a two-level X-ray irradiation system where pallets are arranged on two superposed levels and the x-ray beam is directed along a height corresponding to a distance comprised between mid-height of the lower level up to mid-height of the upper level of said sets of pallets. Pallets are then switched of level for full irradiation.

The solutions of the prior art are adapted to situations where the transport units have a specific shape or have all substantially the same height (h1$i$). In case transport units having different heights need to be treated with such systems, the beam scanning width needs to be adapted to the product height to avoid processing inefficiency. This results in complex scheduling strategies.

The present disclosure offers a simple and easy to implement solution for reducing the DUR in all directions and, in particular, in the vertical axis (Z) of goods contained in transport units of different shapes and dimensions irradiated by X-ray or electron beam. These and other advantages of the present disclosure are described below.

SUMMARY

The present disclosure is defined in the appended claims. In particular, the present disclosure relates to an apparatus for irradiating goods with a radiation selected from X-rays or electron beam, comprising:

a source of radiation selected from X-rays and electron beam, configured for emitting the radiation (11$x$) along an irradiation volume (Xv) centred on an irradiation axis (X), and a conveyor (3) configured for driving the goods loaded in two or more transport units (1.$i$) of unit height (h1$i$) measured along a vertical axis (Z) normal to the irradiation axis (X), along a transverse axis (Y) normal to both irradiation and vertical axes (X), (Z), through the irradiation volume such as to expose a first portion of the goods to the radiation.

The transport units may be loaded in totes of tote height (h5=H51−h50) measured along the vertical axis (Z) from a bottom end located at a bottom end height (h50) to a top end located at a top end height (h51), and the conveyor is configured for driving the totes (5) carrying N transport units loaded with the goods, wherein:

the totes comprise support elements for supporting transport units, wherein the support elements can be positioned at different levels along the tote height (h5) of the totes, and a tote holds N transport units, with N E N and N 1, arranged on top of one another extending over a total height (ht=Ht1−Ht0) measured along the vertical axis (Z) from a bottom of a first transport unit located nearest to the bottom end of the tote at a bottom unit height (Ht0) to a top of an N$^{th}$ transport unit located nearest the top end of the tote at a top unit height (Ht1), and Each transport unit may be held in place in a tote by one or more support elements, such that:

The total height (ht) is comprised between 40% and 100% of the tote height (h5) (i.e., 40% h5 ht h5), or between 60% and 80% of the tote height (h5), The N transport units loaded in a tote span over at least 70%, or at least 80% of the total height (ht)

$$\left(i.e., \sum_{i=1}^{N} h1 \cdot i \geq 70\% \ ht\right),$$

and

The total height (ht) is centred relative to the tote height (h5) within ±20% (i.e., (Ht1−½ ht)=½ h5±20%), or within ±10% (i.e., (Ht1−½ ht)=½ h5±10%).

In some embodiments, the apparatus may comprise a processing control unit (PCS) configured for carrying one or more of the following actions:

measuring the unit height (h1.$i$) of the transport units prior to loading them into totes, weighing the transport units and determining their corresponding densities, determining a target total height (ht0) according to a height of the irradiation volume measured along the vertical axis (Z) and selecting the N transport units to be loaded in each tote to reach a total height (ht) lower than the tote height (h5) and comprised within ±10% of the target total height: (i.e., ht=ht0±10%<h5), for each tote, optimizing the height of the irradiation volume to the total height (ht) of the transport units (1.$i$) loaded in the corresponding totes, determining a loading scheme of the transport units, assigning which transport units are to be loaded in which totes and assigning a loading position of each transport unit in a tote along the vertical axis, according to the unit heights (h1.$i$) of the transport units thus measured, such as to maximize a filling ratio (ht/h5) of the total height (ht) to the tote height (h5), and/or according to the densities thus determined such as the N transport units loaded in a tote have similar densities within ±25%, and assigning a position for each support element optimized according to the unit heights of the transport units to minimize a gap ratio $$\left(\sum_{i}^{N} hvi / ht\right)$$

of a total gap $$\left(\sum_{i}^{N} hvi\right)$$

separating every two adjacent transportation units in a same tote to the total height (ht).

In this embodiment, the apparatus may comprise a loading station configured for loading the transport units onto the totes according to the loading scheme, and in some embodiments, according to the loading position. The loading station can be configured for positioning the support elements at positions optimized according to the unit heights of the transport units to minimize the gap ratio $$\left(\Sigma_i^N hvi / htt\right).$$

Transport units of similar densities may be loaded into one or a series of totes. The conveyor can be configured for driving the one or the series of totes through the irradiation volume at a speed dependent on an average density of the transport units loaded in the one or the series of totes.

The apparatus can comprise a rotating element configured for rotating the totes by an angle of rotation ($\theta$), and the conveyor may be configured for driving several times the totes through the irradiation volume such as to expose second, third, and so on portions of the goods to the radiation each time the totes are rotated by the angle of rotation.

The apparatus can be configured for one level irradiation of the totes, using a scan horn configured for over-scanning such that the irradiation volume includes the whole tote height (h5) and the first portions of the goods of all the N transport units loaded in a tote are exposed to a required dose in a single pass. Alternatively, the apparatus can be configured for two levels irradiation of the totes, using a scan horn configured for under-scanning such that the irradiation volume does not include the whole tote height (h5) and the first portions of the goods of the N transport units loaded in a tote are exposed to the required dose in two passes, with a first pass with a first selection of transport units loaded in an upper half portion of the tote (i.e., above $\frac{1}{2}$ h5), and a second selection of transport units loaded in a lower half portion of the tote (i.e., below $\frac{1}{2}$ h5), and with a second pass with the first selection of transport units loaded in the lower half portion of the tote and the second selection of transport units loaded in the upper half portion of the tote.

If the apparatus is configured for a two-level irradiation, the apparatus may comprise a swapping unit configured for transferring the transport units (1.$i$) loaded in the upper half portion of a first tote to the lower half portion of a second tote (5) and the transport units loaded in the lower half portion of the first tote to the upper half portion of the second tote, and for driving the second tote through the irradiation volume.

The conveyor can be in the form of an elevated track on which the totes (5) are suspended and driven. Alternatively, it can be in the form of a roller conveyor on which the totes (5) stand and are driven.

For two-level systems, the totes can have a tote height (h5) comprised between 500 and 650 cm, for example between 550 and 600 cm. For one-level systems, the tote height (h5) may be lower, such as 290 to 350 cm, for example 300 to 330 cm. A transportation unit can have a unit height (h1$i$) comprised between 50 and 380 cm, for example between 100 and 280 cm. A gap (hvi) separating two adjacent transportation units in a same tote can be comprised between 8 and 30 cm, for example between 15 and 25 cm.

With an apparatus according to the present disclosure, it is possible to yield a dose uniformity ratio (DURx) defined as a ratio (DMx/Dmx) of a maximum dose (DMx) to a minimum dose (Dmx) deposited into a good along the irradiation axis (X) as a function of the vertical axis (Z) between a bottom of the transportation unit and a top of the transportation unit which is not more than 1.4, for example not more than 1.3, or not more than 1.15, for a uniform good density of 0.1 g/cm³.

The present disclosure also relates to a method for irradiating with a radiation selected from X-rays and electron beam goods loaded in transportation units comprising the following steps:

providing an apparatus as defined supra, loading transportation units into the totes provided with the support elements which support the transportation units as defined supra, driving the totes through the irradiation volume, along the transverse axis (Y) to expose the first portion of the goods, and irradiating the transportation units with the radiation as the totes are driven through the irradiation volume.

In some embodiments, after a pass through the irradiation volume to expose a portion of the goods, the totes may be rotated by the rotating angle ($\theta$) and driven back through the irradiation volume, to expose a different portion of the goods contained in the transport units.

In case the conveyor is configured for a two levels irradiation of the totes and the apparatus comprises the swapping unit, the method may comprise:

transferring the transport units loaded in the upper half portion of a first tote to the lower half portion of a second tote and transferring the transport units loaded in the lower half portion of the first tote to the upper half portion of the second tote, and driving the second tote through the irradiation volume (Vx).

The method of the present disclosure has the advantage that a same scanning horn and the irradiation axis (X) can be maintained constant during the whole process irrespective of the heights (h1$i$) of the transport units and of the densities of the goods.

BRIEF DESCRIPTION OF THE FIGURES

For a fuller understanding of the nature of the present disclosure, reference is made to the following detailed description taken in conjunction with the accompanying drawings in which:

FIG. 1($b$): shows a perspective view of a two-level irradiation system according to the state of the art.

FIG. 2($a$): shows the individual components forming a tote according to the present disclosure.

FIG. 2($b$): shows two transport units of different heights (h11 and h12).

FIG. 2($c$): shows the tote of FIG. 2($a$) with support elements in position and loaded with the transport units of FIG. 2($b$).

FIG. 3($a$): shows a two-level system of the state of the art, with various dimensions.

FIG. 3($b$): a tote loaded with two transport units according to the present disclosure with various dimensions.

FIG. 4($b$): shows a perspective view of a second embodiment of irradiation system according to the present disclosure.

FIGS. 5($c$) & 5($d$): show two stages of a two-level irradiation of transport units loaded in a two superimposed tracks conveyor of the state of the art.

FIGS. 5($e$) & 5($f$): show side views of the two stages of the two-level irradiation system according to the present disclosure illustrated in FIGS. 5($a$) & 5($b$).

FIGS. 5(*g*) & 5(*h*): show side views of the two stages of the two-level irradiation system according to the state of the art illustrated in FIGS. 5(*c*) & 5*td*).

FIG. 7(*b*): plots the dose deposition along the irradiation axis (X) upon exposure to a radiation of one portion only (dashed lines, θ=0 and θ=π) and upon exposure of two opposite portions (solid line, M=2).

FIG. 8(*b*): plots the minimum dose (Dmx) deposited along the irradiation axis (X) as a function of the unit height measured along the vertical axis (Z) of a system according to FIG. 8(*a*).

FIG. 8(*c*): plots the DURx along the irradiation axis (X) as a function of the unit height measured along the vertical axis (Z) of a system according to FIG. 8(*a*).

FIG. 9(*a*): shows a side view of a two-level system according to the state-of-the-art FIG. 9(*b*): plots the minimum dose (Dmx) deposited along the irradiation axis (X) as a function of the unit height measured along the vertical axis (Z) of a system according to FIG. 9(*a*).

FIG. 9(*c*): plots the DURx along the irradiation axis (X) as a function of the unit height measured along the vertical axis (Z) of a system according to FIG. 9(*a*).

FIG. 10(*b*): plots DURx along the irradiation axis (X) as a function of the density of the transport units.

DETAILED DESCRIPTION

Figures 1A, 1B:
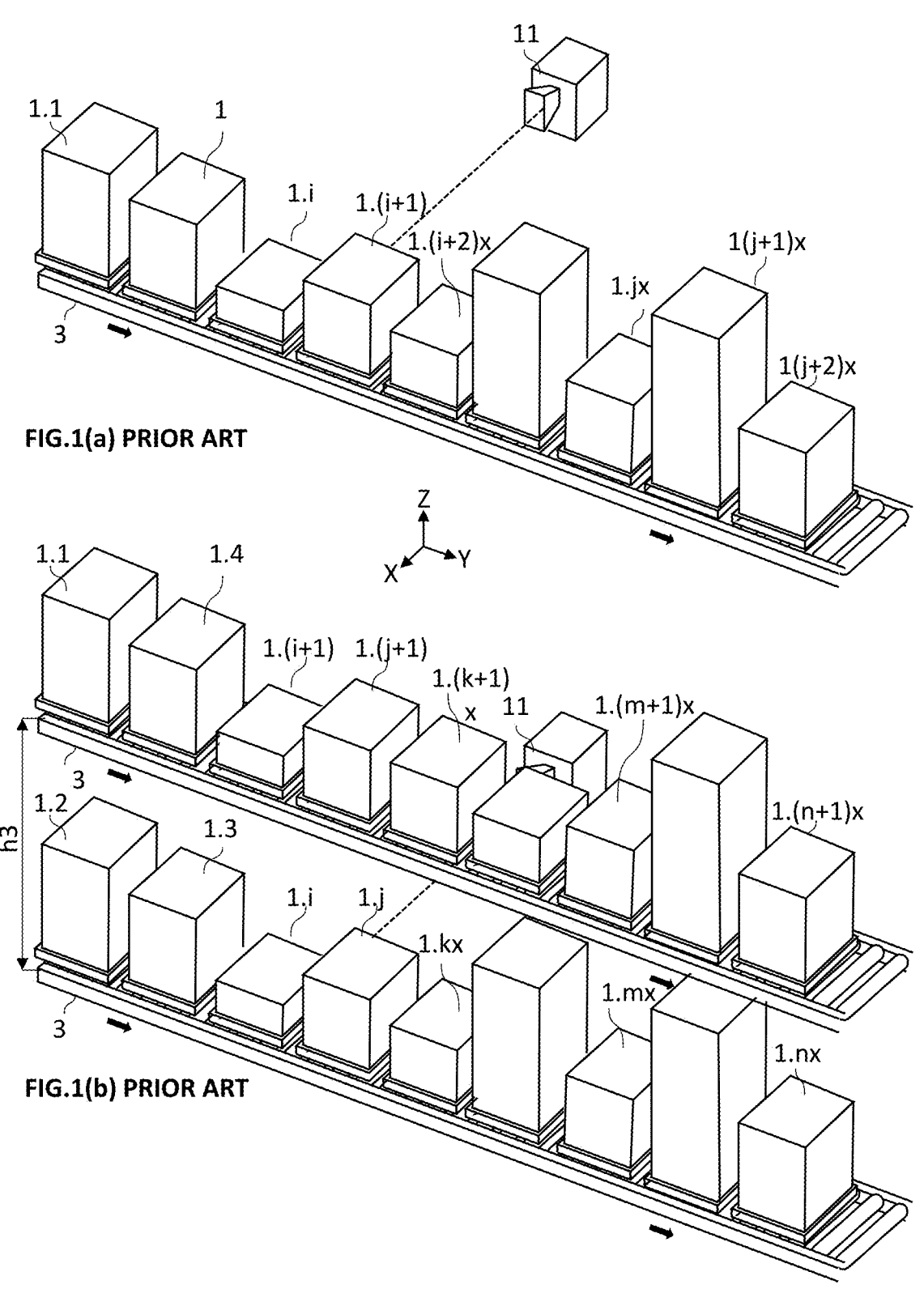
FIG. 1($a$): shows a perspective view of a one-level irradiation system according to the state of the art.
Figures 4A, 4B:
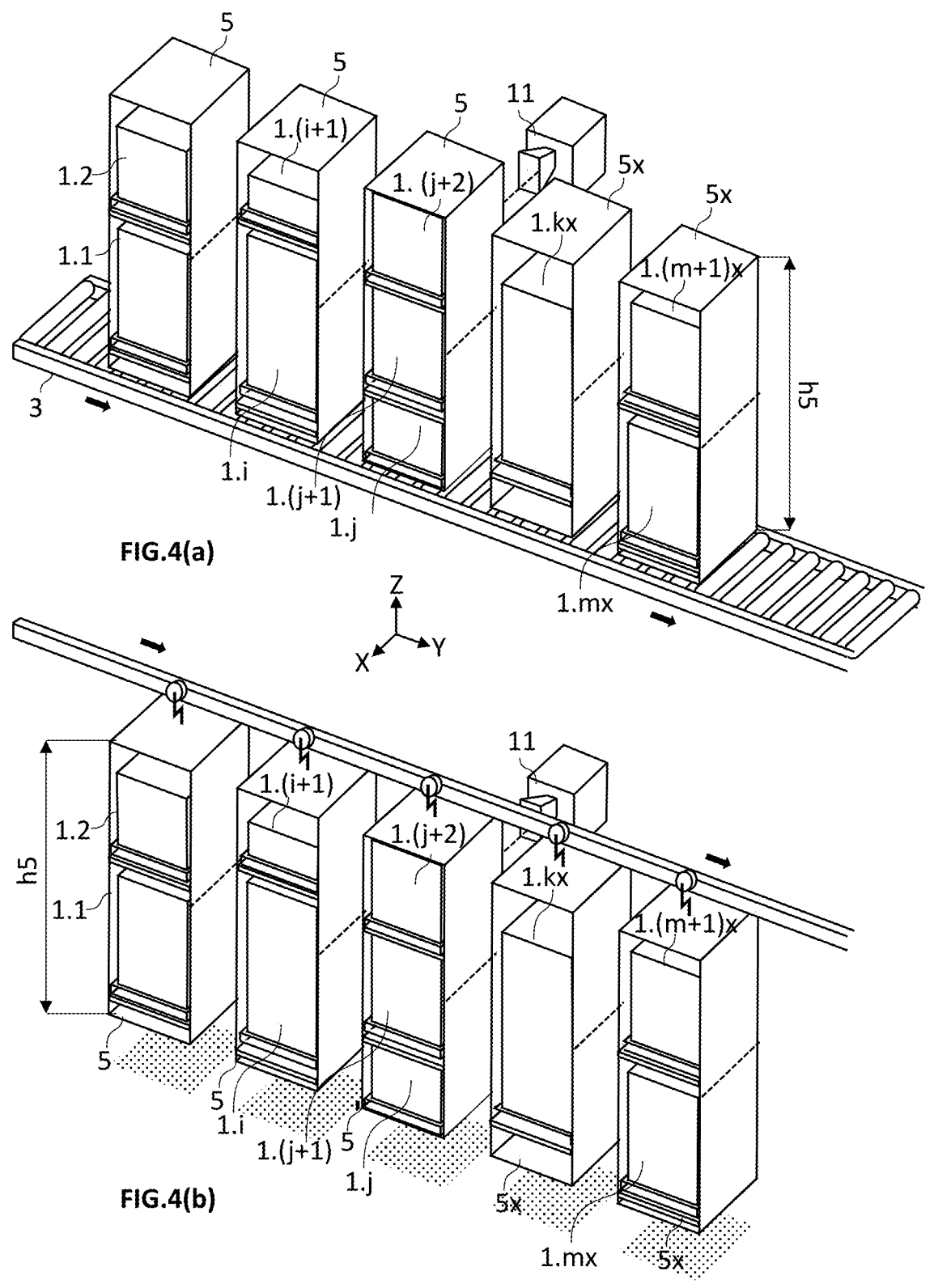
FIG. 4($a$): shows a perspective view of a first embodiment of irradiation system according to the present disclosure.

As illustrated in FIGS. 4(*a*) and 4(*b*), the present disclosure relates to an apparatus for irradiating goods with a radiation (11x) selected from X-rays or electron beam, comprising a source (11) of the radiation (11x) configured for emitting the radiation (11x) along an irradiation volume (Xv) centred on a irradiation axis (X). The goods may be conveyed through the irradiation volume (Xv) supported on or enclosed in transport units (1.*i*) which can be a pallet, a container, a container loaded on a pallet, and the like. A conveyor (3) may be configured for driving the goods loaded in two or more transport units (1.*i*) of unit height (h1*i*) measured along a vertical axis (Z) normal to the irradiation axis (X), along a transverse axis (Y) substantially normal to both irradiation and vertical axes (X), (Z), through the irradiation volume such as to expose a first portion of the goods to the radiation.

The gist of the present disclosure is to load one or more transport units (1.*i*) in totes (5) and to configure the conveyor (3) for driving the totes (5) carrying N transport units (1.*i*) containing the goods through the irradiation volume (Xv), wherein N≥1. The totes may have a tote height (h5=H51– h50) measured along the vertical axis (Z) from a bottom end located at a bottom end height (h50) to a top end located at a top end height (h51). A tote (5) holds N transport units, with N∈N and N≥1, arranged on top of one another extending over a total height (ht=Ht1–Ht0) measured along the vertical axis (Z) from a bottom of a first transport unit (1.1) located nearest to the bottom end of the tote (5) at a bottom unit height (Ht0) to a top of an $N^{th}$ transport unit (1.N) located nearest the top end of the tote at a top unit height (Ht1).

Referring to FIG. 3(*b*), according to the present disclosure, each transport unit (1.*i*) may be held in place in a tote (5) by one or more support elements (5*s*), such that:

the total height (ht) is comprised between 40% and 100% of the tote height (h5) (i.e., 40% h5≤ht≤h5), between 50% and 90%, or between 60% and 80% of the tote height (h5), the N transport units (1.1-1.N) loaded in a tote span over at least 70%

$$\left(\text{i.e., } \sum\nolimits_{i=1}^{N} h1.\, i \geq 70\% \; ht\right),$$

at least 80% of the total height (ht)

$$\left(\text{i.e., } \sum\nolimits_{i=1}^{N} h1.\, i \geq 80\% \; ht\right);$$

in other words, the exposure ratio, $$\sum\nolimits_{i=1}^{N} h1 \cdot i / ht \geq 70\%,$$

or ≥80%; this means that all the gap heights (hvi) measured along the vertical axis (Z) separating a top of a first transport unit and a bottom of an adjacent second transport unit positioned above the first transport unit, do not sum up to more than 30% of the total height (ht)

$$\left(\text{i.e., } \sum\nolimits_{i=1}^{N-1} hvi \leq 30\% \; ht\right),$$

or not more than 20%

$$\left(\text{i.e., } \sum\nolimits_{i=1}^{N-1} hvi \leq 20\% \; ht\right),$$

and the total height (ht) is centred relative to the tote height (h5) within ±20% (i.e., (Ht1–½ ht)=½h5±20%), or within ±10% (i.e., (Ht1–½ ht)=½ h5±10%); this way, the irradiation axis (X) of the source of radiation (11) can be centred about at mid-height of the totes for transport units (1.*i*) of any height (h1*i*).

FIG. 3(*a*) shows a two superimposed track system according to the state of the art, which can be advantageously replaced by the embodiment of FIG. 3(*b*) of the present disclosure.

Transport Units and Totes

The goods to be irradiated can be any type of goods suitable for being treated by radiation. For example, for sterilization processes, the goods can be foodstuff, medicine, medical equipment, electronic components, garments, and the like. For polymerization, crosslinking and shrink fitting, the goods can comprise polymers and polymer precursors. The goods can be stacked on pallets. The goods can be stored in containers made of a material substantially transparent to the radiation. The goods can also be stored in containers standing on pallets. Pallets and containers holding the goods are collectively referred to as transport units ($1.i$), regardless of whether they are open structures or closed containers.

Referring to FIG. 2($b$), transport units may have a substantially standardized footprint on a plane (X, Y) of about 100 to 150 cm per 100 to 150 cm. In Europe, many pallets have standard dimensions of 100×120 cm². The height (h$1i$) along the vertical axis (Z) of the transport units ($1.i$), however, can vary substantially from one unit to another. For example, the unit height (h$1i$) of a transport unit can vary from a few dozen centimetres, e.g., 30 cm to up to 400 cm, or from 50 to 380 cm, or from 100 to 300 cm, or from 120 to 280 cm. The unit height differences between two transport units are one of the reasons of the large variations in values of DURx as a function of the height observed between transport units of different unit heights treated with state-of-the-art installations. Such inhomogeneity of dose deposition between different transport units having been treated similarly is undesirable and, for some applications, unacceptable.

A tote may comprise a structure comprising support elements for holding N transport units one on top of the other. The support elements can be positioned at different levels along the tote height (h5). Totes can be open or closed structures. If the totes are closed structures, the portions exposed to the radiation may be made of a material substantially transparent to X-rays or electron beam. FIG. 2($a$) represents a tote in the form of a semi-open structure with support elements in the shape of shelves. The support elements can have any shape and geometry as long as they are configured for holding in place corresponding transport units at given positions along the vertical axis (Z). Instead of shelves as represented in FIG. 2($a$), the support elements can be in the form of discrete modules, such as pegs, e.g., configured for each supporting a corner of a pallet, or in the form of ledges or rods extending along the irradiation axis (X) or across the transverse axis (Y) for supporting edges of a transport unit. The structure of the tote can be provided with apertures or grooves distributed at different heights along the vertical axis (Z) to accommodate the support elements as discussed supra. FIG. 2($c$) shows the tote of FIG. 2($a$) loaded with the two transport units of FIG. 2($b$). As the support elements ($5s$) can be coupled to the tote at different heights along the vertical axis (Z), it is possible to tailor the positions of the transport units according to any criterion. For example, reducing the gap height (hvi) to reduce the total height (ht) as well as increasing the exposure ratio, $$\sum_{i=1}^{2} h1i/ht,$$

defining a proportion of the total height (ht) filled by goods. It is also possible to move up and down the total height (ht) of transport units along the vertical axis (Z) by varying the values of the distances (hd, hu) separating the bottom and top ends of the tote, respectively, from the transport units adjacent thereto.

N is a natural number and can take any value as long as the total height (ht) remains smaller than the tote height (h5), i.e., ht<h5. FIGS. 4($a$) and 4($b$) illustrate totes loaded with N transport units with N=1, 2, or 3. Higher values of N are possible, with totes carrying 4, 5, or more transport units, as long as the foregoing condition ht<h5 is satisfied.

The footprint of the totes over a plane (X, Y) is adapted for receiving the transport units. As mentioned supra, a standard size of pallets in Europe is 100×120 cm², such that the totes should have a footprint slightly larger than the transport unit footprint, i.e., about 110 to 120 cm per 130 to 140 cm. The tote height (h5) may differ for one-level and two-level systems. In one-level systems irradiation proceeds in an overscan mode, and in two-level systems it proceeds in an underscan mode. Assuming a same scan horn (11$h$) is used having a scanning width (hx) of e.g., 300 cm, measured along the vertical axis (Z), then the total height (ht) of the transport units stacked in a tote will have to be smaller than the scanning width (hx) for one-level systems and larger than the scanning width (hx) for two-level systems.

Although a same tote height (h5) can be used for any value of the total height (ht), if an apparatus is designed for being operated only as a one- or two-level system, the tote height (h5) can be optimized to fit the scanning width (hx) and to the corresponding total height (ht) of transport units ($1.i$) stacked in one tote. For example, assuming N=2 transport units ($1.1$, $1.2$) of unit heights, h$11$=120 cm and h$12$=140 cm, with a gap of height, hv$1$=15 cm, between the two transport units, yields a total height, ht=120+140+15=275 cm. A scan horn having a scanning width hx=300 cm>ht would be suitable for a one-level system. The tote height (h5) could be of the order of 290 to 350 cm, or of 300 to 330 cm for a one-level system. The same applies to a tote ($5$) holding a single transport unit ($1.1$) of unit height of e.g., h$11$=270 cm.

By contrast, a tote height (h5) of the order of 500 to 650 cm, or of 550 to 620 cm, or of 580 to 610 cm may be required for holding N=2 transport units ($1.1$, $1.2$) of heights h$11$=h$12$=270 cm with a gap of height, hv=15 m, yielding a total height of 2×270+15=555 cm. A tote loaded with the two transport units would be suitable for treatment in a two-level system using a scan horn of scanning width, hx=300 cm. The foregoing figures are purely illustrative to give an order of magnitude of the dimensions. They can vary within ±20% without departing from the embodiments of the present disclosure.

As shown with the transport units #($1.j$), ($1.(j+1)$), ($1.(j+2)$) illustrated in FIGS. 4($a$) and 4($b$) a tote can carry more than one or two transport units ($1.i$) depending on the tote height (h5), the unit heights (h$1i$), the gap heights (hv), and the resulting total height (ht), as well as on the scanning width (hx) and the type of one- or two-level system applied to the transport units. The gaps between two adjacent transport units loaded in a tote can have a gap height (hvi) comprised between 8 and 30 cm, or between 12 and 25 cm, or between 15 and 20 cm. N can be any natural number. In a majority of applications, N can be comprised between 1 and 6, or between 2 and 4.

The goods contained in a volume of the transport units ($1.i$) typically have densities comprised between 0.05 to 0.5 g/cm³. The density of the transport units is relevant as absorption of the radiation as it penetrates through the goods increases with density. For this reason, the transport units may be sorted as a function of their densities, and the N transport units loaded in one tote may have similar densities. In some embodiments, batches of several totes may be loaded with transport units of similar densities. This way, the totes of such batches can be driven sequentially through the irradiation volume (Vx) at a constant speed.

Optimization of the Loading of Transport Units (1.$i$) into Each Tote (5)

Figure 11A:
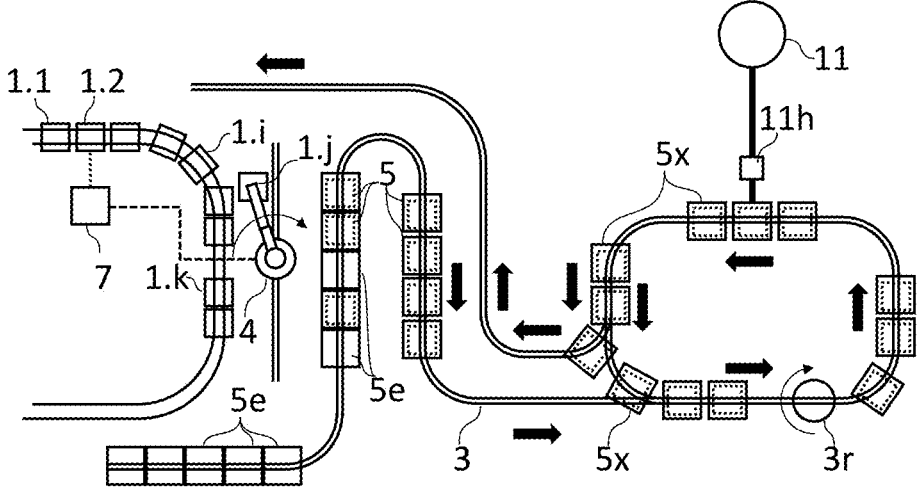
FIGS. 11(*a*) & 11(*b*): show two embodiments of conveyors according to the present disclosure.
Figure 11B:
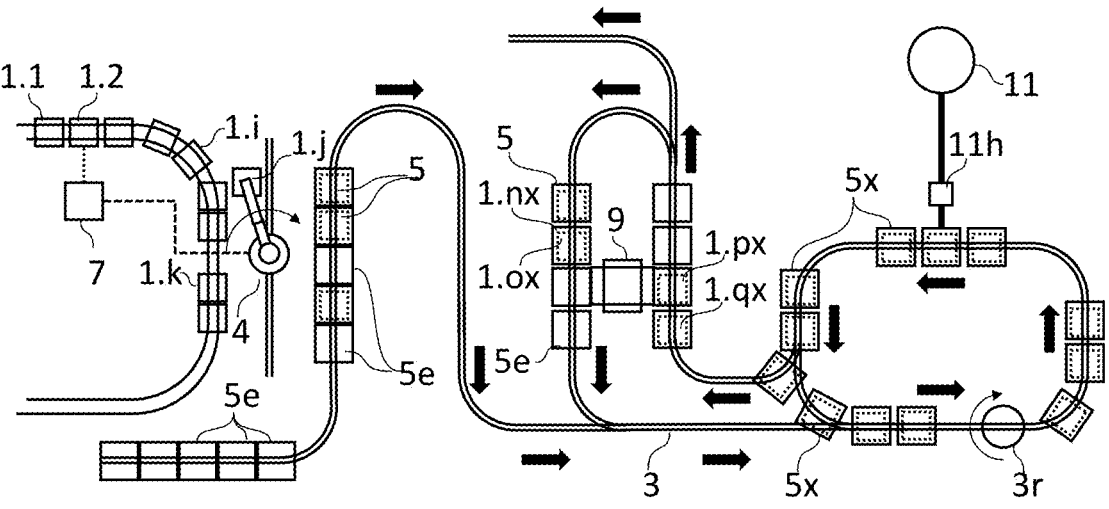

In some embodiments of the present disclosure, the apparatus may comprise a processing control unit (PCS) (7) configured for optimizing the sequence of loading of transport units within a tote and over different totes (5). A PCS (7) can comprise or be coupled to measurement equipment for measuring one or more parameters on the transport units, such as the unit height (h1.$i$), a weight, and/or a density of the transport units (1.$i$). As shown in FIGS. 11($a$) and 11($b$), the measurements can be carried out prior to loading the transport units into totes (5). The PCS can then use the values of the measurements for determining a target total height (ht0) according to a height of the irradiation volume measured along the vertical axis (Z) and selecting the N transport units (1.$i$-1.N) to be loaded in each tote (5) to reach a total height (ht) lower than the tote height (h5) and comprised within ±10% of the target total height: (i.e., ht=ht0±10%<h5). With a same scan horn, it may be possible to vary within a certain range the scanning width (hx) of the irradiation volume measured along the vertical axis (Z). The PCS (7) can be configured for adapting the scanning width (hx) of the irradiation volume to further optimize irradiation of each tote according to the total height (ht) of the N transport units.

The PCS (7) may be configured for determining a loading scheme of the transport units (1.$i$), assigning which transport units (1.$i$) are to be loaded in which totes and assigning a loading position of each transport unit (1.$i$) in a tote along the vertical axis. The totes and loading positions transport units can be assigned, according to the unit heights (h1.$i$) of the transport units thus measured, such as to maximize a filling ratio (ht/h5) of the total height (ht) to the tote height (h5), and/or according to the densities thus determined such that the N transport units (1.1-1.N) loaded in a tote have similar densities within ±25%.

The PCS (7) can also be configured for assigning a position for each support element (5$s$) optimized according to the unit heights of the transport units (1.$i$) to maximize the exposure ratio or, in other words, to minimize a gap ratio $$\left(\sum_{i}^{N-1} hvi / ht\right)$$

of a total gap $$\left(\sum_{i}^{N} hvi\right)$$

separating every two adjacent transportation units (1.$i$, 1.($i$+1)) in a same tote to the total height (ht).

As shown in FIGS. 11($a$) and 11($b$), the PCS (7) may be coupled to a loading station (4). The loading station can be configured for positioning the support elements (5$s$) at positions optimized as discussed above, e.g., according to the unit heights of the transport units (1.$i$) to minimize the gap ratio $$\left(\sum_{i}^{N} hvi / htt\right).$$

The loading station (4) can also be configured for loading the transport units (1.$i$) onto the totes (5) according to the loading scheme, and according to the loading positions in each tote. As shown in FIGS. 11($a$) and 11($b$), a robot can load identified transport units (1.$i$) into corresponding empty totes (5$e$) as optimized by the PCS (7).

The Conveyor (3)

The conveyor (3) can be in the form of an elevated track on which the totes (5) are suspended and driven, as illustrated in FIG. 4($b$). Alternatively, the conveyor (3) can be a roller conveyor on which the totes (5) stand and are driven, as shown in FIG. 4($a$). For reasons of stability, an elevated track may be used for carrying totes of large tote heights (h5), typically used for two-level systems, requiring tote heights of the order of 500 to 620 cm. For lower tote heights, typically used for one-level systems, any one of a roller-conveyor or a suspended track can be used.

Examples of conveyors designs are illustrated in FIGS. 11($a$) and 11($b$). The conveyor can comprise a section for conveying the transport units (1.$i$) individually in front of the PCS (7) for measurements of height, weight, and/or density. A loading station (4) may be coupled to the PCS (7) and may load the individual transport units into corresponding totes at defined positions along the vertical axis (Z) as determined and optimized by the PCS (7). Empty totes (5$e$) may be parked within reach of the loading station (4) waiting for being each loaded with N transport units. The conveyor (3) may drive the loaded totes in front of the source of radiation (11), through the irradiation volume (Vx) at a predefined speed.

In some embodiments, transport units (1.$i$) of similar densities may be loaded into one or a series of totes (5) by the loading station (4) and the conveyor may be configured for driving the one or the series of totes through the irradiation volume at a speed dependent on an average density of the transport units (1.$i$) loaded in the one or the series of totes.

The conveyor (3) may be equipped with a rotating element (3$r$) configured for rotating the totes (5) by an angle of rotation (θ). The conveyor (3) may be configured for driving several times the totes through the irradiation volume such as to expose second, third, and so on portions of the goods to the radiation each time the totes are rotated by the angle of rotation. In some embodiments, θ=180° and the conveyor (3) may drive the totes for a second pass to expose an opposite portion to the one first exposed to the radiation before evacuating the treated totes (5$x$). Alternatively, the rotating element (3$r$) can be located within the irradiation volume (Vx) to rotate the tote as it is being irradiated.

A same structure can be used for conveying the totes in both one-level and two-level systems. The only difference is in a scanning ratio (hx/ht) between the scanning width (hx) of the scan horn and the total height (ht). A scanning ratio hx/ht>1 may define an overscanning mode suitable for one-level systems and a scanning ratio hx/ht<1 may define an underscanning mode suitable for two-level systems.

As shown in FIG. 11($b$), a two-level system may further comprise a swapping unit (9) configured for transferring the transport units (1.$i$) loaded in the upper half portion of a first tote (5) to the lower half portion of a second tote (5) and the transport units (1.$i$) loaded in the lower half portion of the first tote (5) to the upper half portion of the second tote (5), and for driving the second tote through the irradiation volume.

Figures 12A, 12B, 12C, 12D, 12E, 12F, 13A, 13B, 13C, 13D, 13E, 13F:
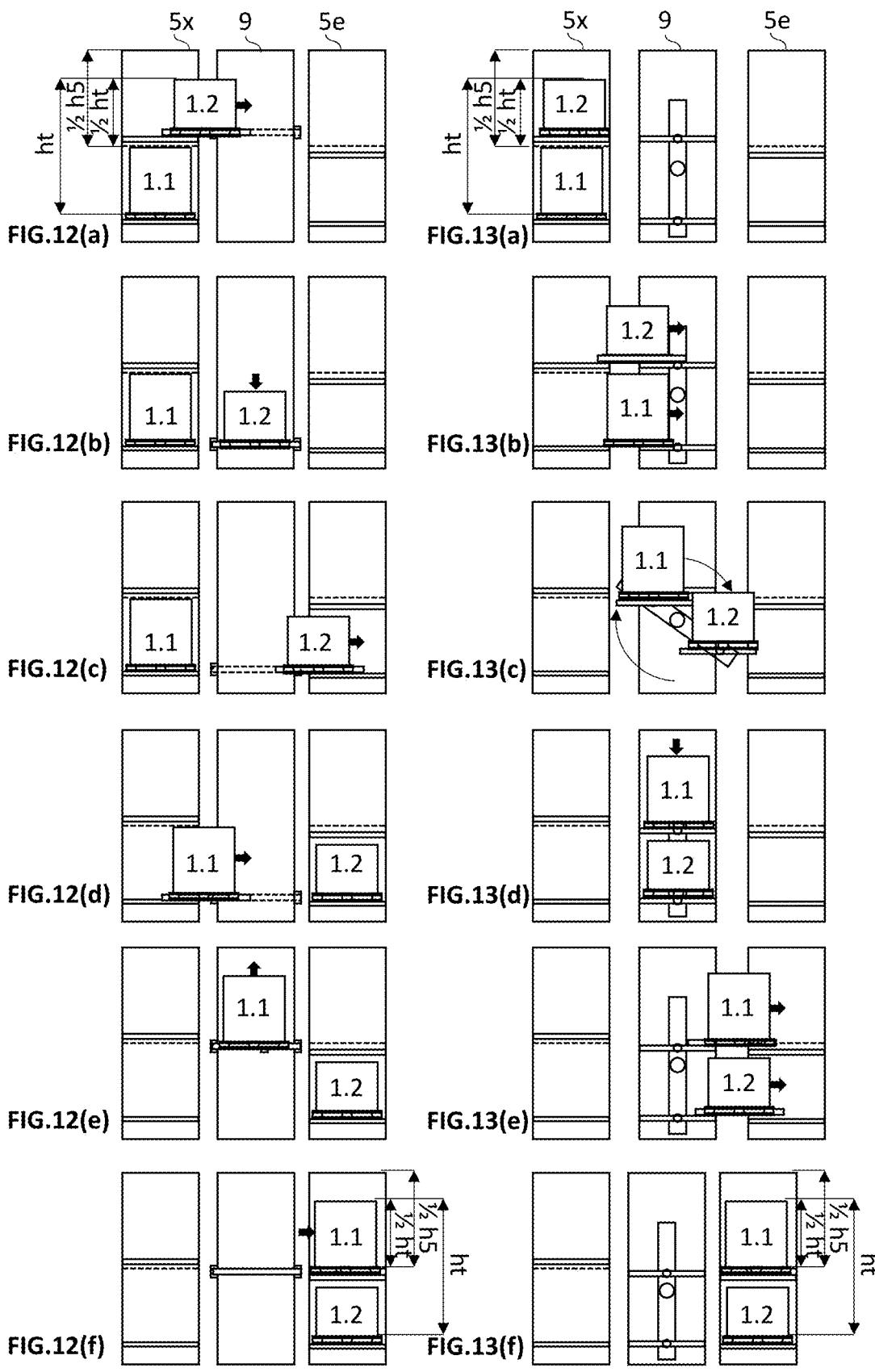
FIGS. 12(*a*) through 12(*f*): show various stages for swapping transport units from a first to a second totes with a first embodiment of swapping unit in a two-level system.
FIGS. 13(*a*) through 13(*f*): show various stages for swapping transport units from a first to a second totes with a second embodiment of swapping unit in a two-level system.

In two-level systems, the PCS (7) can also be configured for optimizing the number and sequence of second totes, as well as the positions of the support elements of the empty second totes (5e) waiting for receiving the transport units (1.*ix*) from the first totes (5x) after a first exposure to the radiation. The empty second totes may be parked vis-à-vis the first totes (5x), with the support elements (5s) at the corresponding positions for swapping the transport units up-down and down-up. As illustrated in FIGS. 12(*a*) through 12(*f*), the swapping unit (9) can be in the form of an elevator configured for retrieving a first transport unit of a first tote (5x) (cf. FIG. 12(*a*)), bringing the first transport unit to its corresponding new position along the vertical axis (Z) assigned thereto in the empty second tote (cf. FIG. 12(*b*)), and then loading the transport unit into the second tote at the predefined position assigned thereto (cf. FIG. 12(*c*)). The same operation may be repeated with each transport unit remaining in the first tote (cf. FIGS. 12(*d*) through 12(*f*).

In another embodiment illustrated in FIGS. 13(*a*) through 13(*f*), the swapping unit may comprise two rotating arms each provided with handling means for retrieving from, holding, and loading into a tote a transport unit. The position of the handling means along the respective arms can be varied. As shown in FIG. 13(*a*), the two arms may be first held vertically, and the handling means levelled with corresponding transport units to be swapped. The two handling means may retrieve the two transport units (cf. FIG. 13(*b*)) and the two arms may rotate about the central axis by an angle of 180° to bring the transport units facing their respective newly assigned positions in the second tote (cf. FIGS. 13(*c*) and (*d*)). If required, the positions of the handling means carrying the two transport units can be varied to face the corresponding new positions in the second tote. The handling means can load their respective transport units into the second tote at their newly assigned positions (cf. FIGS. 13(*e*) and 13(*f*)).

These operations may be repeated for each transport unit loaded in a first tote, for all the first totes having received the first-level irradiation. The second totes thus loaded may be ready for driving the transport units through the irradiation volume (Vx) to receive the second-level irradiation of the two-level system. The empty first totes can be evacuated and refurbished before being reloaded with a new set of N transport units. The number and positions of the support elements can be adapted to the new load of transport units as explained supra.

One-Level System

Figures 5A, 5B, 5C, 5D:
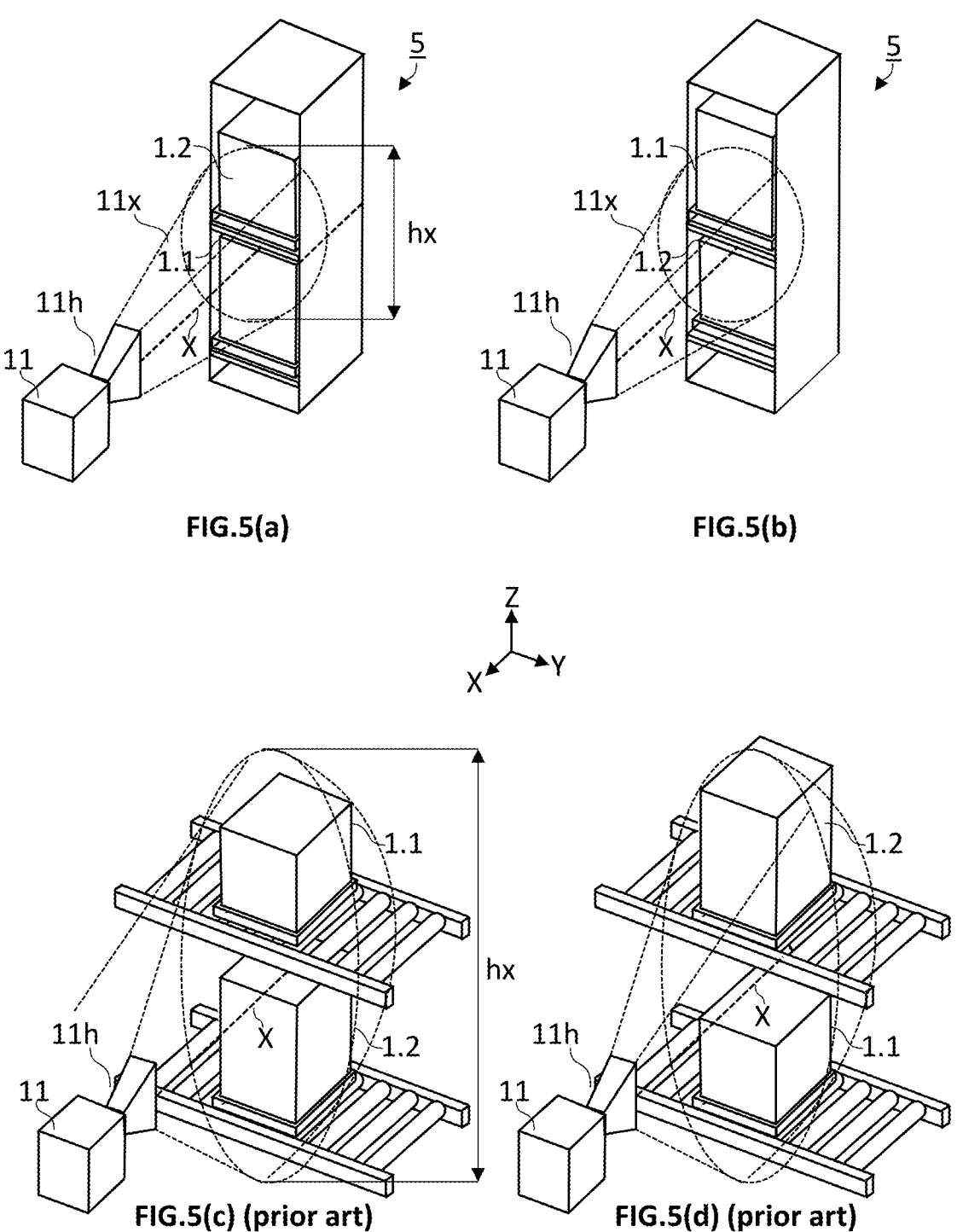
FIGS. 5($a$) & 5($b$): show two stages of a two-level irradiation of transport units loaded in totes according to the present disclosure.
Figures 5E, 5F, 5G, 5H, 6A, 6B:
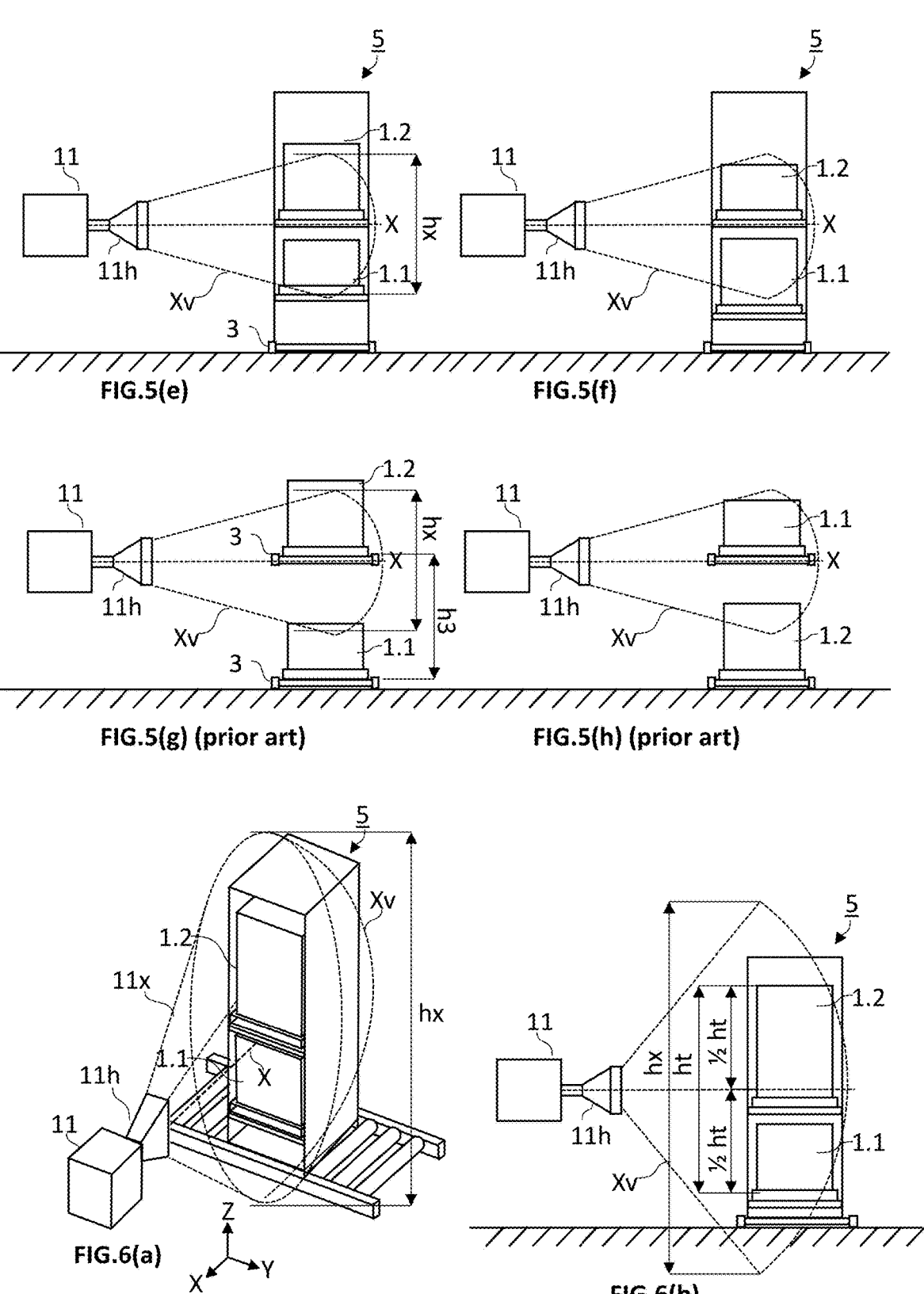
FIGS. 6(*a*) & 6(*b*): show a perspective view and a side view of a one-level irradiation of transport units loaded in totes according to the present disclosure.

As explained supra and as illustrated in FIGS. 6(*a*) and 6(*b*), one-level systems may irradiate the transport units in an overscanning mode, with a scanning width (hx) larger than the total height (ht) of the transport units (1.*i*) (i.e., hx/ht>1). The cost of a scan horn (11) may increase more than linearly with the scanning width (hx) it affords. There may therefore be a financial drive to keep the scanning width (hx) within reasonable sizes, to limit the cost of the installation. One-level systems may be used for transport units stacked in totes over a total height (ht) of the order of not more than 300 cm (i.e., ht<300 cm). For example, assuming a scan horn having a scanning width, hx=300 cm, and allowing for an overscan of about 15 cm both below and above the transport units (1.*i*), the tote (5) could carry N transport units over a total height of the order of 270 cm.

A one-level system may be simpler to operate than two-level systems and may be faster than a two-level system. Actually, the process throughputs of one-level systems and two-level systems are not so different for the following reasons. Although the transport units loaded in a tote in a two-level system may pass a second time through the irradiation volume (Vx), the total height (ht) of transport units being driven through the irradiation volume (Vx) in one pass of a two-level system can be about the double of the total height (ht) in a one-level system.

Figure 7A:
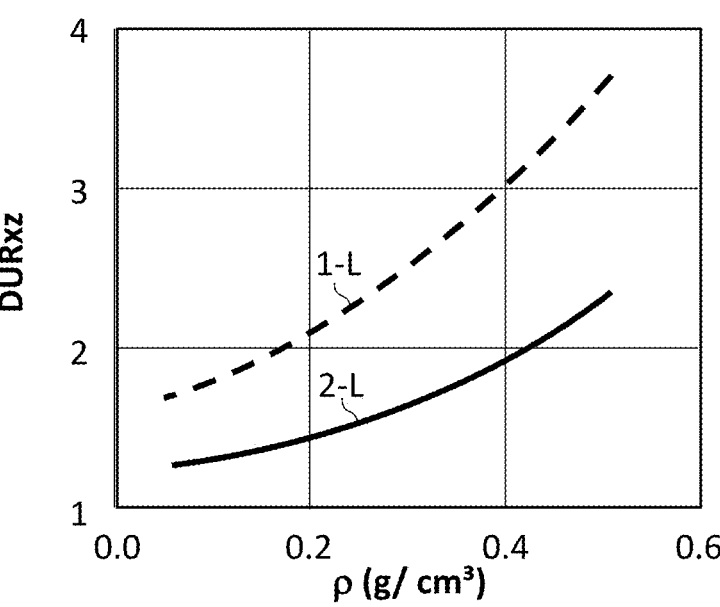
FIG. 7(*a*): shows a graph of the DURxz along the plane (X, Z) as a function of the density of the transport units for a one-level system (1-L) and a two-level system (2-L).
Figure 7B:
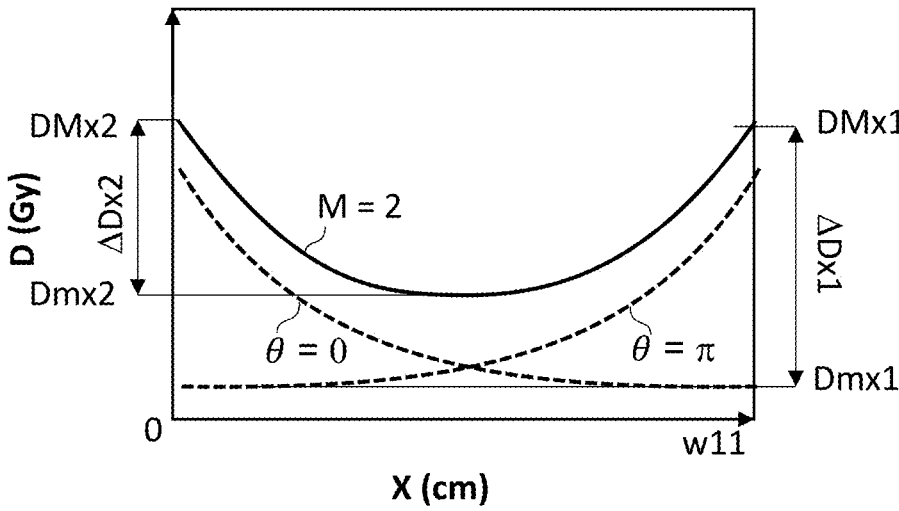

FIG. 7(*a*) compares calculated values of DURxz along a plane (X, Z) as a function of the transport unit density (ρ) obtained with one-level systems (dashed line) and two-level systems (solid line), obtained with a one-level system irradiating totes carrying a single transport unit (1.1) of unit height, h11=260 cm, and with a two-level system irradiating totes carrying two transport units (1.1, 1.2) each of unit height, h11=h12=260 cm separated from one another by a gap of height, hv=15 cm. The scanning width, hx=300 cm. FIG. 7(*a*) shows that the DURxz obtained with a one-level system is higher (poorer) than the DURxz obtained with a two-level system.

Two-Level System

As illustrated in FIGS. 5(*a*) & 5(*b*) and in FIGS. 5(*e*) & 5(*f*), in a two-level system, the transport units loaded in a tote may be irradiated twice, with a swap of the transport units (1.*i*) between the top and bottom half portions of the totes between the two passes. As discussed supra in reference with FIGS. 12 and 13(*a*) through (*f*), the swap of the transport units (1.*i*) between the top and bottom portions of the tote can be carried out with a swapping unit (9) located between a first tote (5x) which was previously driven through the irradiation volume (Vx), and a second tote (5e) which is empty and ready to receive the transport units from the first tote. The swapping unit (9) collects a first transport unit (1.1) from a top half portion of the first tote, lowers the first transport unit to a level of the bottom half portion of the totes and transfers the first transport unit (1.1) to the bottom portion of the second tote. The operation can be repeated as often as necessary to transfer all the transport units from the first tote to the second toe. The foregoing operations can be carried out in any sequence desired by the operator. The thus newly loaded second tote can be driven for a second pass of the transport units through the irradiation volume (Vx).

Though not mandatory, in two-level systems, the totes may comprise a support element (5s) located to within ±30 cm, or within ±20 cm, or within ±10 cm, or within ±5 cm from a half-height (½h5) of the tote, defined as a plane normal to the vertical axis (Z) located at equal distance (½ h5) from both bottom end and the top end. This way, the swap of transport units between bottom and top half portions of the totes may allow depositing during the second pass a second pass dose which is complementary with the first pass dose deposited during the first pass, and thus yielding a lower value of DUR. At the same time, care should be taken to centre the total height (ht) approximately on the irradiation axis (X). The support elements (5s) in the second tote may therefore not necessarily be at the same levels as in the first tote.

In case a tote is loaded with transport units of similar heights, the support elements (5s) of the second tote can simply be located at the same positions as in the first tote. In case, however, transport units of different heights are loaded in a tote, as shown in FIGS. 12 and 13 (*a*) through (*f*), with two transport units (1.1, 1.2) of different unit heights (h11, h12). the positions of the support elements (5s) of the second tote may have to be different from their positions in the first tote. In another example, in case the top half portion of the first tote carries a first transport unit (1.1) of unit height (h11) and the bottom half height is loaded with second and third transport units (1.2, 1.3) of unit heights (h12, h13), with h12+h13≈h11, the first tote comprises a single (set of) support element (5s) on the top half portion to support the first transport unit (1.1) whilst the bottom half portion is provided with two (sets of) support elements (5s) for supporting the second and third transport units (1.2, 1.3). Upon swapping the transport units, the second tote may comprise two (sets of) support elements (5s) on the top half portion thereof for supporting the second and third transport units (1.2, 1.3), and a single (set of) support element (5s) on the bottom half portion to support the first transport unit (1.1). The processing control unit (PCS) (7) can be configured for ensuring that the second tote be provided with the support elements (5s) at the required positions for operating the swap of transport units in the best conditions and as rapidly as possible.

Because the totes (5) for two-level systems usually have large tote heights (h5) of the order of 500 to 650 cm, for stability issues, the totes (5) may be driven with a conveyor (3) comprising an elevated track on which the totes (5) are suspended.

Dose Deposition Distribution Along the Irradiation Axis (X)

The dose deposition distribution along the irradiation axis (X) into a transport unit (1.i) by a radiation (11x) is illustrated in FIG. 7(*b*). In order to decrease the difference, ΔxDx1=DMx1−Dmx1, between DMx1 and Dmx1, obtained by exposing one portion only of the transport units (cf. dashed line and dotted line in FIG. 7(*b*)), the transport units may be irradiated from different orientations. In one embodiment illustrated in FIGS. 11(*a*) and 11(*b*), the conveyor may comprise a rotating element (3r) remote from the irradiation volume (Vx) for rotating the tote by and angle θ=2π/M rad and after each rotation for again driving the totes (5) (M−1) times through the irradiation volume (Vx) for a total of M passes. In practice, M can be equal to 2, with θ=2π, thus exposing diametrically opposed surfaces of the transport units with two passes. By comparing in FIG. 7(*b*), ΔDx1 obtained by irradiating one portion only of the transport unit (dashed lines, M=1, "θ=0" and "θ=π") with ΔDx2 obtained by irradiating two opposite portions (solid line, "M=2"), it can be seen that two passes with a rotation of θ=πsubstantially improve the homogeneity of the dose deposition distribution along the irradiation axis (X). The treatment time is, however, prolonged accordingly, as rotating and passing a second time the totes is time-consuming.

In an alternative embodiment, the rotating element may be located within the irradiation volume, such that each tote (5) rotates continuously or intermittently about the vertical axis (Z) as it stands within the irradiation volume (Vx). For example, the conveyor may comprise a rotating element configured for rotating (M— 1) times a tote by an angle θ=2π/M rad to successively expose M portions of the transport units (1.i) loaded in the tote to the irradiation volume (Vx). This solution yields the same advantages in terms of enhanced homogeneity as discussed supra in relation with FIGS. 11(*a*) and 11(*b*).

In yet another embodiment, the apparatus may comprise a second source of radiation configured for emitting a radiation along a second irradiation volume centred on a second irradiation axis such as to irradiate a second portion of the transport units (1.i). The second irradiation axis may be parallel to, or coaxial with the first irradiation axis (X), and irradiation proceeds in a direction opposite to the irradiation by the first source of radiation (11). This way, two opposite portions of the transport units can be irradiated simultaneously, thus increasing the throughput accordingly. This solution is, however, substantially more expensive than the previous ones, as it requires a second source of radiation.

Two-Level Systems Using Totes (5) Vs State-of-the-Art Double Track Systems

The gist of the present disclosure applied to two-level systems, wherein transport units (1.i) are stacked one on top of the other in totes rather than on two superimposed tracks (3) separated from one another by a separation distance (h3) is that the distribution of the transport units can be varied and optimized, minimizing the gaps (hvi) between adjacent transport units (1.i, 1.(*i*+1)). This has several advantages.

First, the total gap height (Σ,hvi)) can be minimized. The larger the total gap height, the larger the amount of wasted energy. In state-of-the-art superimposed tracks, the single gap height (hv1) cannot be controlled and depends on the unit height (h11) of the transport unit (1.1) loaded in the lower track as hv1=h3−h11. The waste of energy due to the larger gap height (hv1) in the state-of-the-art superimposed tracks is illustrated for a two-level system, on the one hand, In FIG. 10(*a*) plotting the minimum dose (Dmx) deposited along the irradiation axis (X) for all positions along the vertical axis (Z) as a function of the density of the transport units and, on the other hand, by comparing the minimum dose (Dmx) deposited along the irradiation axis (X) as a function of the position along the vertical axis (Z) into two superimposed transport units (1.1, 1.2) of same unit height, h11=h12=100 cm, loaded in a tote (5) according to the present disclosure as plotted in FIG. 8(*b*) (solid line) with the same two transport units (1.1, 1.2) loaded in two state-of-the-art superimposed tracks in FIG. 9(*b*) (solid line).

Figure 8A:
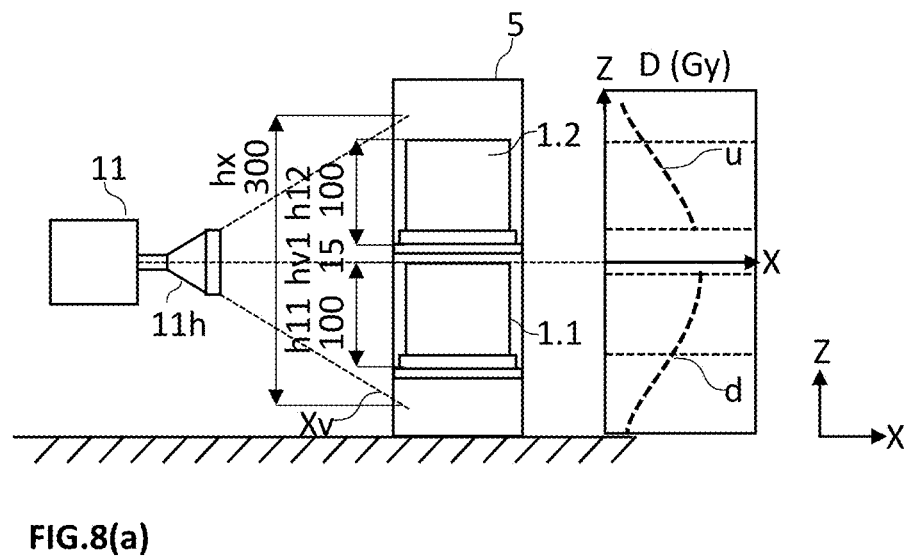
FIG. 8(*a*): shows a side view of a two-level system according to the present disclosure.
Figure 8B:
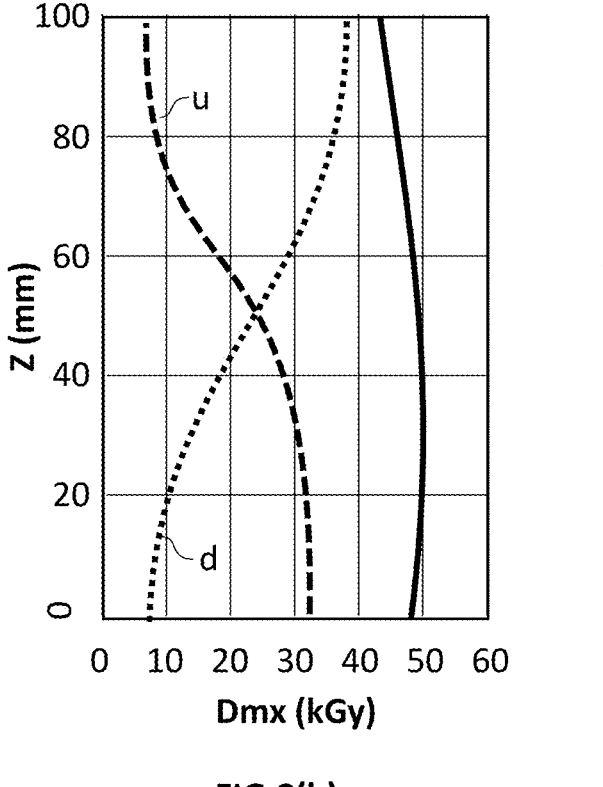
Figure 8C:
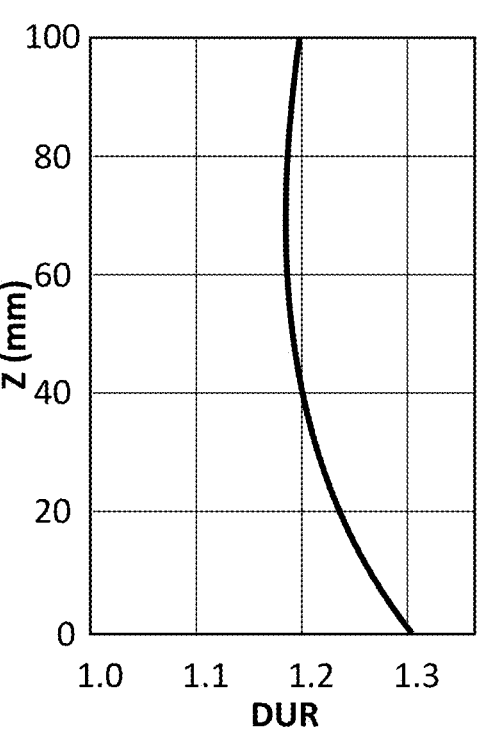

It can be seen from FIGS. 8(*b*) and 9(*b*), that for the same irradiation beam (here a 7 MeV X-ray beam), a total minimum dose Dmx comprised between 40 and 50 kGy may be deposited into each transport unit when loaded in a tote minimizing the gap height (hv1=15 cm) whilst the total minimum dose Dmx deposited into each transport unit loaded in the superimposed tracks is comprised between 20 and 30 kGy only. The difference of deposited doses between the two is wasted in the state-of-the-art superimposed track. The same conclusion can be reached from FIG. 10(*a*) by comparing the solid line according to the present disclosure with the dashed line according to the state-of-the-art two superimposed track system. It follows that with an apparatus according to the present disclosure, either a lower energy radiation source (11) can be used thus decreasing the cost of the source of radiation (11), or the totes can be driven through the irradiation volume (Vx) at a higher rate, thus increasing the throughput. In both cases, substantial saving in energy, time, and cost can be generated with the present disclosure. The total minimum dose Dmx represented by the solid lines in FIGS. 8(*b*) and 9(*b*) are the sum of the minimum doses deposited along the irradiation axis (X) into a transport unit (1.1) when positioned in the lower half portion of the tote or the lower track (dotted line, "d"=down) and when positioned in the upper half portion of the tote or the upper track (dashed line, "u"=up).

Second, with state-of-the-art two superimposed tracks the number N of transport units which can be stacked on top of one another is limited to N=2 for all unit heights (h1i) lower than the separation distance (h3) between the two tracks (i.e., ∀Vh1i<h3). By using totes according to the present disclosure, more than two transport units can be stacked on top of one another as long as the total height (ht) remains lower than the tote height (h5) (i.e., ht<h5).

For example, two superimposed tracks separated from one another by a separation distance, h3=300 cm can be compared with a tote (5) of tote height, h5=600 cm. If transport units (1.i) of unit height, h1i=120 cm must be treated, two transport units can be irradiated at a time with the two superimposed tracks, with a gap height, hv1=300–120=180 cm. The exposure ratio, $$\sum\nolimits_{i=1}^{2} h1i/ht,$$

defining the proportion of goods distributed along the total height (ht) is equal to $2 \times 120/(2 \times 120+180)=57\%$ of the total height. This means that 43% of the total height (ht) is made of gaps, thus wasting 43% of the energy of the emitted radiation.

With a tote of tote height, h5=600 cm, four transport units of unit height, h1$i$=120 cm, can be loaded in one tote, with hv$i$=15 cm gaps between every two transportation units, yielding a total gap height, $$\sum\nolimits_{i=1}^{3} hvi, = 3 \times 15 \text{ cm} = 45 \text{ cm}$$

only, with an exposure ratio, $$\sum\nolimits_{i=1}^{4} h1i/ht = 4 \times 120/(4 \times 120 + 3 \times 15) = 91\%$$

of the total height filled by goods during irradiation. Only 9% of the total height (ht) is made of gaps. This example illustrates the advantage of the present disclosure over the state-of-the-art superimposed tracks systems, yielding a throughput twice as high with four transport units being irradiated at each pass instead of two for the superimposed tracks, and with an exposure ratio which is 34% higher, yielding a corresponding saving of energy.

Figure 10A:
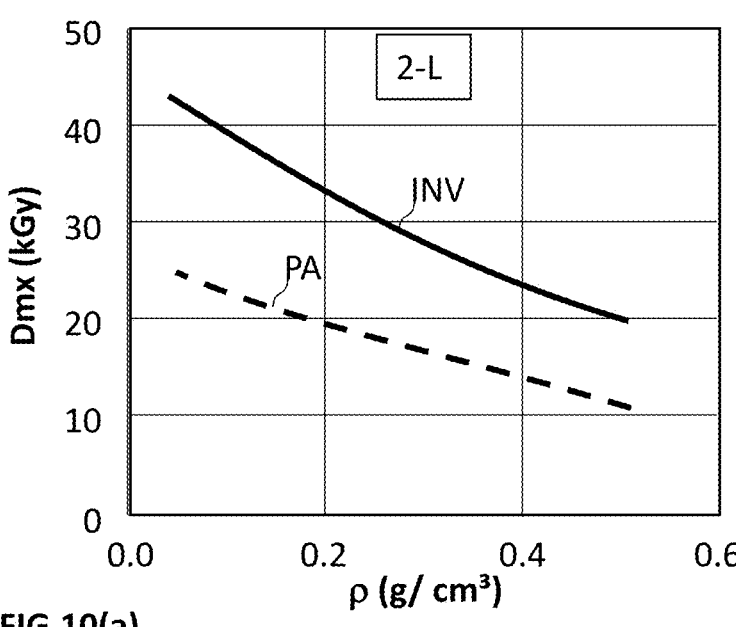
FIG. 10(*a*): plots the minimum dose (Dmx) deposited along the irradiation axis (X) as a function of the density of the transport units.
Figure 10B:
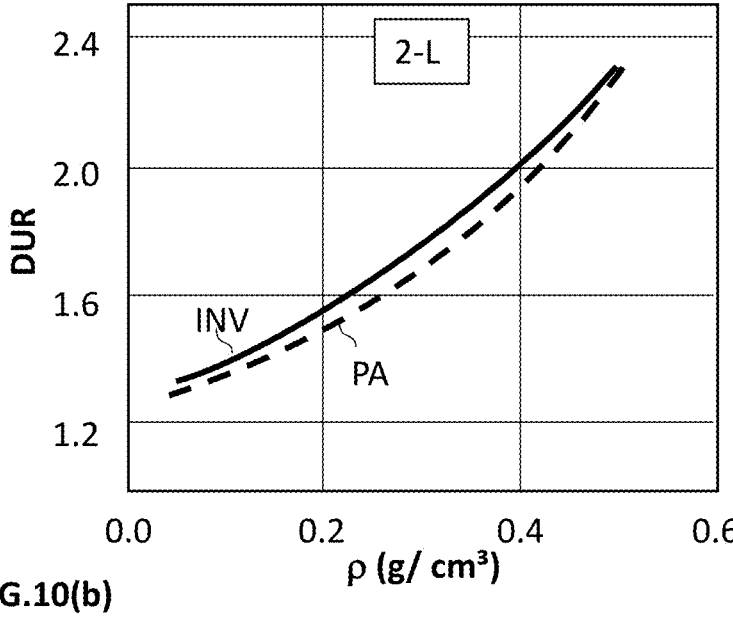

FIGS. 8($c$) and 9($c$) plot the values of DURx along the irradiation axis (X) as a function of the unit height (h1$i$) measured along the vertical axis (Z). It can be seen that in both tote and superimposed tracks, the values of DURx=DMx/Dmx, are lower than 1.3, which is quite acceptable. FIG. 10($b$) plots the values of DURx along the irradiation axis (X) as a function of the density of the transport units density in the two-level systems discussed with reference to FIGS. 8 and 9, according to the present disclosure (solid line) and a two-superimposed track system (dashed line). It can be seen that the values of the DURx according to the present disclosure maintain the values of DURx obtained with a two superimposed tracks installation.

According to the present disclosure, the dose uniformity ratio (DURx) defined as the ratio (DMx/Dmx) of the maximum dose (DMx) to a minimum dose (Dmx) deposited into a good along the irradiation axis (X) as a function of the vertical axis (Z) between a bottom of the transportation unit (1.$i$) and a top of the transportation unit (1.$i$) may not be more than 1.4, or not more than 1.3, or not more than 1.15, for a uniform good density of 0.1 g/cm$^3$.

Third, by using totes, a suspended track can be used to drive the totes loaded with transport units through the irradiation volume (Vx) rather than using motorized roller conveyors as in conventional installations. A suspended track is advantageous because it requires less moving and motorized parts exposed to the aggressive environment within and in the area surrounding the irradiation volume (Vx). Unlike roller conveyors, a suspended track drives the totes by means of a chain or a cable which is pulled by a motor which can be located well remote from the irradiation volume (Vx), thus prolonging the service life of the equipment, and reducing the number of failures requiring stopping the conveyor. Note that roller conveyors can be used with the present disclosure if desired.

Method for Irradiating Goods with a Radiation

The apparatus of the present disclosure can advantageously be used in a method for irradiating with a radiation selected among X-rays and electron beam goods contained in transport units (1.$i$). The method may comprise the following steps:

providing an apparatus as discussed supra, loading transportation units (1.$i$) onto the totes (5) provided with the support elements (5$s$) which support the transportation units (1.$i$) as discussed supra, driving the totes (5) through the irradiation volume centred on the irradiation axis (X), along the transverse axis (Y) to expose a first portion of the goods, and irradiating the transportation units (1.$i$) with the radiation (11$x$) as the totes (5) are driven through the irradiation volume.

To decrease the value of DURx, after a pass through the irradiation volume to expose a portion of the goods, the thus irradiated totes (5$x$) may be rotated by the rotating angle (θ) and driven back through the irradiation volume, to expose a different portion of the goods contained in the transport units (1.$i$). Alternatively, the totes can be rotated within the irradiation volume (Vx).

In some embodiments, the method may apply a two-level irradiation of the totes (5) and the apparatus may comprise a swapping unit (9) as discussed supra. In this embodiment, the method may comprise the steps of:

transferring the transport units (1.$i$) loaded in the upper half portion of a first tote (5) to the lower half portion of a second tote (5) and transferring the transport units (1.$i$) loaded in the lower half portion of the first tote (5) to the upper half portion of the second tote (5), and driving the second tote through the irradiation volume (Vx).

The present disclosure has the advantage that all irradiation parameters including the radiation energy, the scanning horn (11$h$), and the irradiation axis (X) can be maintained constant during the whole process for irradiating transport units of different unit heights (h1$i$) and densities. The driving rate of the totes through the irradiation volume (Vx) may be adapted to the densities of the transport units loaded in each tote (5).

The throughput can be increased compared with state-of-the-art installations, as more than two transport units can be loaded in one tote, as long as the total height (ht) remains smaller than the tote height (h5) (i.e., ht<h5).

As the total gap height, $$\sum\nolimits_{i}^{N-1} hvi,$$

can be reduced, and the exposure ratio, $$\sum\nolimits_{i=1}^{N} h1i/ht,$$

increased accordingly, the efficacy of the process is substantially enhanced compared with a state-of-the-art two superimposed tracks system, with less radiation wasted through the gap between two transportation units.

The apparatus and method of the present disclosure can be applied for both one-level and two-level irradiation techniques.

A higher minimum dose (Dmx) can be deposited with an apparatus according to the present disclosure as with state-of-the-art apparatuses using a same source of radiation (11).

The invention claimed is:

1. An apparatus for irradiating goods with X-ray or electron beam radiation, the apparatus comprising:

a radiation source configured to emit radiation along an irradiation volume centered around an irradiation axis, wherein the radiation comprises X-rays or an electron beam;

a conveyor configured to drive two or more transport units, along a transverse axis through the irradiation volume to expose the goods in the two or more transport units to the radiation, wherein each of the two or more transport units has a unit height along a vertical axis normal to the irradiation axis, and the transverse axis is normal to the irradiation axis and the vertical axis; and a plurality of totes each having a tote height along the vertical axis and configured to hold the two or more transport units;

wherein:

one of the plurality of totes holds at least one of the two or more transport units extending over a total height along the vertical axis, the conveyor is configured to drive the two or more transport units by driving the plurality of totes carrying the two or more transport units containing the goods, the plurality of totes comprise support elements for supporting the two or more transport units, wherein:

the support elements are positioned at different levels along the tote height of the plurality of totes, to adapt a distance separating two adjacent support elements along the vertical axis, the support elements are configured to be positioned at the different levels to tailor positions of the two or more transport units in the plurality of totes based on the unit heights of the two or more transport units, the total height is between 40% and 100% of the tote height, the at least one transport unit spans over at least 70% of the total height in the one of the plurality of totes, and the total height is centered relative to the tote height within ±20%.

2. The apparatus of claim 1, further comprising a processing control unit configured to perform at least one of:

measuring the unit height of the two or more transport units prior to loading the two or more transport units into the plurality of totes;

weighing the two or more transport units and determining corresponding densities of the two or more transport units;

determining a target total height according to a height of the irradiation volume measured along the vertical axis and selecting the N transport units to be loaded in each tote to reach a total height lower than the tote height and comprised within ±10% of the target total height, optimizing, for each of the plurality of totes, the height of the irradiation volume to the total height of at least one of the two or more transport units loaded in a corresponding one of the plurality of totes;

determining a loading scheme of the two or more transport units, assigning which of the two or more transport units are to be loaded in which of the plurality of totes, and assigning a loading position of each of the two or more transport units in a corresponding one of the totes along the vertical axis according to at least one of:

unit heights of the two or more transport units, to maximize a filling ratio of the total height to the tote height, or densities of at least one of the two or more transport units in the corresponding tote, to have similar densities within ±25%; or assigning a position for each of the support elements according to the unit heights of the two or more transport units to minimize a gap ratio of a total gap separating every two adjacent transport units in a same tote to the total height.

3. The apparatus of claim 1, further comprising:

a rotating element configured for rotating the plurality of totes by an angle of rotation, wherein the conveyor is configured to drive the plurality of totes through the irradiation volume a plurality of times to expose a plurality of portions of the goods to the radiation, wherein the plurality of totes are rotated by the angle of rotation in each of the plurality of times.

4. The apparatus of claim 1, further comprising one of:

a first scan horn coupled to the radiation source for one-level irradiation of the plurality of totes, wherein the radiation source with the first scan horn is configured to over-scan such that the irradiation volume entirely covers the tote height and first portions of the goods of at least one of the two or more transport units in the corresponding tote are exposed to a required dose in a single pass; or a second scan horn coupled to the radiation source for two-level irradiation of the plurality of totes, wherein the radiation source with the second scan horn is configured to under-scan such that the irradiation volume does not entirely cover the tote height and the first portions of the goods of the at least one transport unit in the tote are exposed to the required dose in two passes, a first of the two passes being with a first selection of the at least one transport unit in an upper half portion of the tote and a second selection of the at least one transport unit in a lower half portion of the tote, and a second of the two passes being with the first selection of the at least one transport unit in the lower half portion of the tote and the second selection of the at least one transport unit in the upper half portion of the tote.

5. The apparatus of claim 1, further comprising:

a swapping unit configured to transfer one or more of the at least one transport unit in an upper half portion of a first of the plurality of totes to a lower half portion of a second of the plurality of totes and one or more of the at least one transport unit in a lower half portion of the first of the plurality of totes to an upper half portion of the second of the plurality of totes for driving the second of the plurality of totes through the irradiation volume.

6. The apparatus of claim 1, wherein the conveyor comprises;

an elevated track on which the plurality of totes are suspended and driven, or a roller conveyor on which the plurality of totes stand and are driven.

7. The apparatus of claim 1, wherein:

the tote height is between 500 and 650 centimeters (cm), the unit height is between 50 and 380 cm, and a gap separating two adjacent transport units of the two or more transport units in a same tote is between 8 and 30 cm.

8. The apparatus of claim 1, wherein a dose uniformity ratio is a ratio of a maximum dose to a minimum dose deposited, by the radiation source, into a good along the irradiation axis as a function of the vertical axis between a bottom of one of the two or more transport units and a top of the one of the two or more transport units, and the dose uniformity ratio is not more than 1.4 for a uniform good density of 0.1 g/cm³.

9. The apparatus of claim 2, further comprising:
a loading station configured to load the two or more transport units into the plurality of totes according to at least one of the loading scheme or the loading position.

10. The apparatus of claim 2, wherein:
ones of the two or more transport units of similar densities are loaded into one or a series of the plurality of totes, and
the conveyor is configured to drive the one or the series of the plurality of totes through the irradiation volume at a speed dependent on an average density of the two or more transport units of similar densities in the one or the series of the plurality of totes.

11. The apparatus of claim 9, wherein the loading station is further configured to position each of the one or more support elements at positions according to the unit heights of the two or more transport units to minimize the gap ratio.

12. A method for irradiating goods with radiation of X-ray or an electron beam, the method comprising:
loading the goods into a plurality of transport units, each of the plurality of transport units having a unit height along a vertical axis,
coupling support elements to a plurality of totes at different heights along the vertical axis, to tailor positions for the plurality of transport units based on unit heights of the plurality of transport units,
loading the plurality of transport units into the plurality of totes and supporting the plurality of transport units at the positions by the support elements;
driving the plurality of totes through an irradiation volume, along a transverse axis normal to the vertical axis to expose a portion of the goods in the plurality of transport units; and
irradiating the plurality of transport units with the radiation as the plurality of totes are driven through the irradiation volume.

13. The method of claim 12, wherein the portion of the goods is a first portion of the goods, the method further comprising:
rotating the plurality of totes by a rotating angle, and
driving back the plurality of totes through the irradiation volume, to expose a second portion of the goods in the plurality of transport units to the radiation.

14. The method of claim 12, further comprising:
transferring one or more of the plurality of transport units in an upper half portion of a first of the plurality of totes to a lower half portion of a second of the plurality of totes;
transferring one or more of the plurality of transport units in a lower half portion of the first of the plurality of totes to an upper half portion of the second of the plurality of totes; and
driving the second of the plurality of totes through the irradiation volume.

15. The method of claim 12, further comprising:
maintaining constant a scanning horn of a radiation source and an irradiation axis of the irradiation volume during a whole process of the irradiation.

* * * * *